(12) United States Patent
Smith et al.

(10) Patent No.: US 7,696,203 B2
(45) Date of Patent: Apr. 13, 2010

(54) DNA-PK INHIBITORS

(75) Inventors: Graeme Cameron Murray Smith, Cambridge (GB); Niall Morrison Barr Martin, Cambridge (GB); Keith Allan Menear, Cambridge (GB); Marc Geoffrey Hummersone, Cambridge (GB); Xiao-ling Cockcroft, Cambridge (GB); Mark Frigerio, Cambridge (GB); Roger John Griffin, Newcastle upon Tyne (GB); Bernard Thomas Golding, Newcastle upon Tyne (GB); Ian Robert Hardcastle, Newcastle upon Tyne (GB); David Richard Newell, Newcastle upon Tyne (GB); Hilary Alan Calvert, Newcastle upon Tyne (GB); Nicola Jane Curtin, Newcastle upon Tyne (GB); Kappusamy Saravanan, Bangalore (IN); Marine Desage-El Murr, Paris (FR)

(73) Assignees: Kudos Pharmaceuticals Limited, Cambridge (GB); Cancer Research Technology Limited, London (GB)

( * ) Notice: Subject to any disclaimer, the term of this patent is extended or adjusted under 35 U.S.C. 154(b) by 990 days.

(21) Appl. No.: 11/403,606

(22) Filed: Apr. 13, 2006

(65) Prior Publication Data
US 2006/0264427 A1 Nov. 23, 2006

Related U.S. Application Data

(60) Provisional application No. 60/671,830, filed on Apr. 15, 2005, provisional application No. 60/671,886, filed on Apr. 15, 2005, provisional application No. 60/696,064, filed on Jul. 1, 2005, provisional application No. 60/718,904, filed on Sep. 20, 2005.

(30) Foreign Application Priority Data
Apr. 18, 2005 (GB) .................. 0507831.6

(51) Int. Cl.
A61K 31/535 (2006.01)
C07D 413/14 (2006.01)
(52) U.S. Cl. .................. 514/232.5; 544/119
(58) Field of Classification Search .............. 514/232.5; 544/119
See application file for complete search history.

(56) References Cited

U.S. PATENT DOCUMENTS

| | | |
|---|---|---|
| 4,954,518 A | 9/1990 | Takano et al. |
| 5,252,735 A | 10/1993 | Morris |
| 5,284,856 A | 2/1994 | Naik et al. |
| 5,302,613 A | 4/1994 | Morris |
| 5,703,075 A | 12/1997 | Gammill et al. |
| 5,733,920 A | 3/1998 | Mansuri et al. |
| 5,922,755 A | 7/1999 | Tanaka et al. |
| 6,348,311 B1 | 2/2002 | Kastan et al. |
| 6,387,640 B1 | 5/2002 | Kastan et al. |
| 7,049,313 B2 | 5/2006 | Smith et al. |

(Continued)

FOREIGN PATENT DOCUMENTS

| | | |
|---|---|---|
| EP | 0 610 519 A1 | 8/1994 |
| EP | 0 635 268 A1 | 1/1995 |
| EP | 0 640 339 A1 | 3/1995 |
| EP | 0 641 566 A1 | 3/1995 |
| EP | 0 648 492 A2 | 4/1995 |
| EP | 0 658 343 A1 | 6/1995 |
| GB | 1303724 | 1/1973 |
| GB | 2 302 021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |

(Continued)

OTHER PUBLICATIONS

Byrn et al., Solid-State Chemistry of Drugs, Second Edition, 1999, pp. 233-247.*

(Continued)

*Primary Examiner*—Rebecca L Anderson
(74) *Attorney, Agent, or Firm*—Michael Best & Friedrich LLP

(57) ABSTRACT

Compounds of formula I:

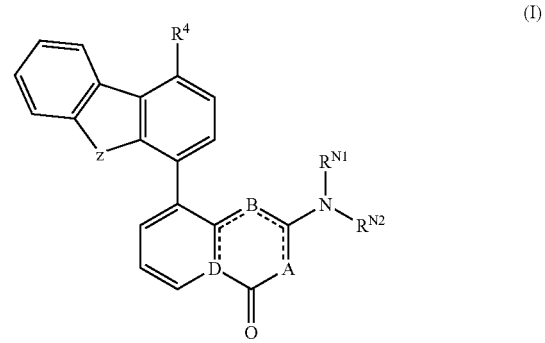

wherein A, B and D are respectively selected from the group consisting of:
(i) CH, NH, C;
(ii) CH, N, N; and
(iii) CH, O, C;
the dotted lines represent two double bonds in the appropriate locations;
and where Z is selected from S, O, C(=O), $CH_2$ and NH are disclosed for use in inhibiting DNA-PK.

9 Claims, No Drawings

U.S. PATENT DOCUMENTS

| | | | |
|---|---|---|---|
| 7,056,942 | B2 | 6/2006 | Hildesheim et al. |
| 2004/0023968 | A1 | 2/2004 | Martin et al. |
| 2004/0192687 | A1 | 9/2004 | Martin et al. |
| 2005/0054657 | A1 | 3/2005 | Smith et al. |
| 2005/0107367 | A1 | 5/2005 | Martin et al. |
| 2006/0106025 | A1 | 5/2006 | Smith et al. |
| 2006/0178361 | A1 | 8/2006 | Hummersone et al. |
| 2006/0264623 | A1 | 11/2006 | Smith et al. |
| 2007/0238729 | A1 | 10/2007 | Martin et al. |
| 2007/0238731 | A1 | 10/2007 | Smith et al. |
| 2008/0242664 | A1 | 10/2008 | Smith et al. |
| 2009/0042865 | A1 | 2/2009 | Frigerio |
| 2009/0043091 | A1 | 2/2009 | Smith et al. |

FOREIGN PATENT DOCUMENTS

| | | |
|---|---|---|
| WO | WO 95/29673 | 11/1995 |
| WO | WO 96/01108 | 1/1996 |
| WO | WO 97/15658 | 5/1997 |
| WO | WO 97/18323 | 5/1997 |
| WO | WO 98/55602 | 12/1998 |
| WO | WO 98/56391 | 12/1998 |
| WO | WO 99/47494 | 9/1999 |
| WO | WO 01/53266 A1 | 7/2001 |
| WO | WO 02/20500 A2 | 3/2002 |
| WO | WO 02/056912 A2 | 7/2002 |
| WO | WO 03/024949 A1 | 3/2003 |
| WO | WO 03/093261 | 4/2003 |
| WO | WO 03/034997 A2 | 5/2003 |
| WO | WO 03/035618 A2 | 5/2003 |
| WO | WO 03/070726 | 8/2003 |
| WO | WO 2006/032869 | 3/2006 |

OTHER PUBLICATIONS

United States Patent Office Action for U.S. Appl. No. 11/351,052 dated Feb. 23, 2009 (10 pages).
United States Patent Office Action for U.S. Appl. No. 11/351,052 dated Aug. 15, 2008 (8 pages).
United States Patent Office Action for U.S. Appl. No. 11/351,052 dated Nov. 26, 2007 (8 pages).
United States Patent Office Action for U.S. Appl. No. 11/351,052 dated Jun. 13, 2007 (11 pages).
United States Patent Office Action for U.S. Appl. No. 10/373,114 dated Aug. 31, 2004 (15 pages).
United States Patent Office Action for U.S. Appl. No. 10/373,114 dated Mar. 30, 2005 (5 pages).
United States Patent Office Action for U.S. Application No. 10/918,180 dated Jun. 6, 2007 (12 pages).
United States Patent Office Action for U.S. Appl. No. 10/918,180 dated Dec. 5, 2007 (6 pages).
United States Patent Office Action for U.S. Appl. No. 10/486,811 dated Sep. 19, 2005 (4 pages).
United States Patent Office Action for U.S. Appl. No. 10/486,811 dated Jan. 5, 2006 (4 pages).
United States Patent Office Action for U.S. Appl. No. 11/231,041 dated Jul. 19, 2007 (13 pages).
Abraham, Robert T., "Cell cycle checkpoint signaling through the ATM and ATR kinases," Genes & Dev., 15: 2177-2196 (2001).
Archer, S. et al., "Ring-Hydroxylated Analogues of Lucanthone as Antitumore Agents," J. Med Chem., 25, 220-227 (1982).
Banin, S., et al., "Enhanced phosphorylation of p53 by ATM in response to DNA damage," Science, 281:1674-1677 (1998).
Bantick, J.R., et al., "Synthesis of 2-aminochromones," J. Heterocyclic Chem, 1981, vol. 18, pp. 679-684.
Berge, Stephen M., et al., "Review article," J. Pharm. Sci., 66:1, pp. 1-19 (1977).
Bettoni, et al., "Synthesis and absolute configuration of substituted morpholines," Tetrahedron, 1980, vol. 36, pp. 409-415.
Boyd, J., et al., "The chemistry of the 'insoluble red' woods," J. Chem. Soc., 1948, pp. 174-176.
Brown, P.O., "Integration of retroviral DNA," Curr Top Microbiol Immunol., 157:19-48 (1990).
Buon, C., et al., "Synthesis of 3-substituted and 2,3-disubstituted-4H-1,4-Benzoxazines," Tetrahedron, 2000, vol. 56, pp. 604-614.
Chiosis, G, et al. "LY294002-geldanamycin heterodiamers as selective inhibitors of the PI3K and PI3k-related family", Bioorganic & Medicinal Chemistry Letters, vol. 11, No. 7, Apr. 9, 2001 pp. 909-913, XP004232522.
Daniel, R., et al., "A role for DNA-PK in retroviral DNA integration," Science, 1999, vol. 284, pp. 644-647.
Daniel, Rene, et al., "Wortmannin potentiates integrase-mediated killing of lymphocytes and reduces the efficiency of stable transduction by retroviruses," Mol. Cell Biol, 21:4, 1164-1172 (2001).
Datta, A., et al., "Reformatsky reaction on aroylketene S, N-acetals: a facile route to 4-amino-6-aryl-2H-pyran-2-ones," Synthesis, 1988, vol. 3, pp. 248-250.
Di Braccio, M., et al., "1,2-fused pyrimidines VII," Eur. J. Med., Chem., 1995, vol. 30, No. 1, pp. 27-38.
Di Braccio, M., et al., "Pyran derivatives XIX. (Dialkylamino) substituted 1-benzopyranones and naphthopyranoes with platelet antiaggregating activity," Farmaco, 1995, vol. 50, No. 10, pp. 703-711.
Durocher, Daniel, and Jackson, Stephen P., "DNA-PK, ATM and ATR as sensors of DNA damage: variations on a theme?," Curr Opin Cell Biol., 13:225-231 (2001).
Ermili, A., et al., "Chemical and pharmacological research on pyran derivatives," Enclosed: Chemical Abstracts, 1977, vol. 87, No. 15, p. 588 (XP-002218602), 117750g.
Gell, D., et al., "Mapping of protein-protein interactions within the DNA-dependent protein kinase complex," Nucleic Acid Res., 1999, vol. 27, No. 17, pp. 3494-3502.
Giroux, A., et al, "One pot biaryl synthesis via in situ boronate formation," Tet. Lett., 38:22, 3841-3844 (1997).
Goytisolo, et al., "The absence of DNA-dependent protein kinase catalytic subunit in mice results in anaphase bridges and in increased telomeric fusions with normal telomere length and G-strand overhang," Mol. Cell. Biol., 2001, vol. 21, No. 11, pp. 3642-3651.
Greene, T. and Wuts, P., ed., *Protective Groups in Organic Synthesis*, Wiley (1999).
Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Human Tumor Cell Line in Vitro", J. Med. Chem., 2005, 48, 569-585.
Hartley, K. O., et al., "DNA-dependent protein kinase catalytic subunit: a relative of phosphatidylinositol 3-kinase and the ataxia telengiectasia gene product," Cell, 1995, vol. 82, pp. 849-856.
Haselhorst, Dorte, et al., "Development of cell lines stably expressing human immunodeficiency virus type 1 proteins for studies in encapsidation and gene transfer," J Gen Virol, 79: 231-237 (1998).
Herzog, Karl-Heinz et al.,"Requirement for ATM in ionizing radiation-induced cell death in the developing central nervous system," Science, 280: 1089-1091 (1998).
Hickson, Ian, et al, "Identification and Characterization of a Novel and Specific Inhibitor of the Ataxia-Telangiectasia Mutated Kinase ATM," Cancer Research 64, Dec. 15, 2004, 9152-9159.
Hollick, J J, et al., "2,6-Disubstituted pyran-4-one and thiopyran-4-one inhibitors of DNA-dependent protein kinase" Bioorganic and Medicinal Chemistry Letters, vol. 13, No. 18, Sep. 15, 2003 pp. 3083-3086, XP002303369.
Ishiyama, T. et al., "Synthesis of arylboronates via the palladium(0)-catalyzed cross-coupling reaction of tetra(alkoxo)diborons with aryl triflates," Tett. Lett., 38:19, 3447-3450 (1997).
Ismail, I.H. et al., "SU11752 inhibits the DNA-dependent protein kinase and DNA double-strand break repair resulting in ionizing radiation sensitization," Oncogene (2004) 23:873-883.
Izzard, R.A., et al., "Competitive & noncompetitive inhibition of the DNA-dependent protein kinase," Cancer Research, 1999, vol. 59, No. 11, pp. 2581-2586.
Jackson, S. P., "DNA damage detection by DNA dependent protein kinase and related enzymes," Cancer Surv., 1996, vol. 28, pp. 261-279.
Jung, J. C., et al., "Simple and cost effective synthesis of 4-hydroxycoumarin," Synth. Commun., 1999, vol. 29, No. 20, pp. 3587-3595.

Kashishian, A. et al., "DNA-dependent protein kinase inhibitors as drug candidates for the treatment of cancer," Mol. Cancer Ther. (2003) 2:1257-1264.

Keith, Curtis T. and Schreiber, Stuart L., "PIK-related kinases: DNA repair, recombination, and cell cycle checkpoints," Science, 270: 50-51 (1995).

Knight, A.R., et al., "Isolation and characterization of 4-chloro-3,4'; 3',4"-tercoumarin," Can. J. Chem., 1968, vol. 46, pp. 2495-2499.

Kubik, et al., "Fine tuning of the cation affinity of artificial receptors based on cyclic peptides by intramolecular conformational control," Eur. J. Org. Chem., 2001, pp. 311-312.

Lau et al., "Suprression of HIV-1 infection by a small molecule inhibitor of the ATM kinase," Nature Cell Biology (2005) 7:493-500.

Lavin, Martin F. and Shiloh, Yosef, "The genetic defect in ataxia-telangiectasia," Annu. Rev. Immunol, 15:177-202 (1997).

Leahy, et al., "Identification of a highly potent and selective DNA-dependent protein kinase (DNA-PK) inhibitor (NU7441) by screening of chromenone librariest", Bioorganic & Medicinal Chemistry Letters 14 (2004) 6083-6087.

Metcalfe, Judith A. et al., "Accelerated telomere shortening in ataxia telangiectasia," Nature Genetics, 13: 350-353 (1996).

Mlotkowska, B.L. et al., "Two-dimensional NMR studies of 2-substituted thioxanthene sulfoxides," J. Heterocyclic Chem., 28: 731-736 (Apr.-May 1991).

Morris, J., et al., "Synthesis and biological evaluation of antiplatelet 2-aminochromones," J. Med. Chem., 1993, vol. 36, No. 14, pp. 2026-2032.

Morris, J., et al., "Synthesis of 2-amino-6-phenyl-4H-pyran-4-ones," Synthesis, 1994, pp. 43-46.

Morris, J., et al., "Reaction of phosgeniminium salts with enolates derived from Lewis acid complexes of 2'-hydroxypropiophenones and related β-Diketones," J. Org. Chem., 1996, vol. 61, No. 9, pp. 3218-3220.

Muller, C. et al., "DNA-dependent protein kinase activity correlates with clinical and in vitro sensitivity of chronic lymphocytic leukemia lymphocytes to nitrogen mustards," Blood (1998) 92:2213-2219.

Naldini, Luigi et al., "In vivo gene delivery and stable transduction of nondividing cells by a lentiviral vector," Science, 272: 263-267 (1996).

Oh, C., et al., "Nucleophilic vinylic substitution of halocoumarins and halo-1,4-napthoquinones with morpholine," J. Heterocyclic Chem., 1994, vol. 31, pp. 841-843.

Remington's Pharmaceutical Sciences, 18th ed., Mack Pub. Co., Easton, PA (1990).

Roma, G., et al., "Synthesis, antiplatelet activity and comparative molecular field analysis of substituted 2-amino-4H pyrido[1,2-a]pyrimidin-4-ones, their congeners and isosteric analogues," Bioorganic & Medicinal Chemistry, 2000, vol. 8, pp. 751-768.

Roma, G., et al., "Pyran derivatives XX. 2-aminochromone benzo-fused derivatives with antiproliferative properties," II Farmaco, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," Clin. Cancer Res., 1997, vol. 3, 1149-1156.

Sarkaria, Jann N. et al., "Inhibition of ATM and ATR kinase activities by the radiosensitizing agent, caffeine," Cancer Res., 59: 4375-4382 (1999).

Savitsky, Kinneret et al., "A single ataxia telangiectasia gene with a product similar to P1-3 kinase," Science, 268:1749-1753 (1995).

Schroth, W., et al., "2,4,6-Tris(dialkylamino) pyrylium salts and related systems, synthesis and reaction behavior," Tetrahedron Letters, 1988, vol. 29, No. 37, pp. 4695-4698.

Schroth, W. et al., "2,4,6-Tris(dialkylamino) pyrylium salts and related systems, synthesis and reaction behavior," Chemical Abstracts, 110:135031.

Shiloh, Yosef, "ATM and ATR: networking cellular responses to DNA damage," Curr. Opin. Genet. Dev., 11:71-77 (2001).

Sirzen, F. et al., "DNA-dependent protein kinase content and activity in lung carcinoma cell lines: correlation with intrinsic radiosensitivity," Eur. J. Cancer (1999) 35:111-116.

Skehan, P., et al., "New colorimetric cytotoxicity assay for anticancer-drug screening," J. Natl. Cancer Inst., 1990, vol. 82, No. 13, pp. 1107-1112.

Smith, G. C. M., etal., "The DNA-dependent protein kinase," Genes & Dev., 1999, vol. 13, pp. 916-934.

Snyder, et al., "Structure and reactions of malonyl-α-aminopyridine. I," J. Am. Chem. Soc., 1952, vol. 74, pp. 4910-4914.

Ten Hoeve, et al., "Direct substitution of aromatic ethers by lithium amides. A new aromatic amination reaction," J. Org. Chem., 1993, vol. 58, pp. 5101-5106.

Toker, Alex and Cantley, Lewis C., "Signalling through the lipid products of phosphoinositide-3-OH kinase," Nature, 387:673-676 (1997).

Veuger, S. J., et al., "Radiosensitization and DNA repair inhibition by the combined use of novel inhibitors of DNA-dependent protein kinase and poly (ADP-ribose) polymerase-1," Cancer Research, 2003, vol. 63, pp. 6008-6015.

Vlahos, C. J., et al., "A specific inhibitor of phosphatidylinositol 3-kinase, 2-(4- morpholinyl)-8-phenyl-4H-1-benzopyran-4-one (LY294002)," J. Biol. Chem., 1994, vol. 269, No. 7, pp. 5241-5248.

Willmore et al., "A novel DNA-dependent protein kinase inhibitor, NU7026, potentiates the cytotoxicity of topoisomerase II poisons used in the treatment of leukemia", Blood, Jun. 15, 2004, vol. 103, No. 12, 4659-4665.

Wymann, M. T., et al., "Wortmannin inactivates phosphoinositide-3-kinase by covalent modification of Lys-802, a residue involved in the phosphate transfer reaction," Mol. Cell Biol., 1996, vol. 16, No. 4, pp. 1722-1733.

Zaikian, Virginia A., "ATM-related genes: What do they tell us about functions of the human gene?" Cell, 82:685-687 (1995).

United States Patent Office Action for U.S. Appl. No. 11/758,332 dated Mar. 25, 2009 (10 pages).

United States Patent Office Action for U.S. Appl. No. 11/403,763 dated Apr. 29, 2009 (9 pages).

* cited by examiner

DNA-PK INHIBITORS

CROSS-REFERENCE TO RELATED APPLICATIONS

This application claims the priority benefits of U.S. Provisional Patent Application Ser. Nos. 60/671,830 filed on Apr. 15, 2005, 60/671,886 filed on Apr. 15, 2005, 60/696,064 filed on Jul. 1, 2005 and 60/718,904 filed on Sep. 20, 2005, and claims the foreign priority benefits of United Kingdom Patent Application No. 0507831.6 filed on Apr. 18, 2005.

The present invention relates to compounds which act as DNA-PK inhibitors, their use and synthesis.

The DNA-dependent protein kinase (DNA-PK) is a nuclear serine/threonine protein kinase that is activated upon association with DNA. Biochemical and genetic data have revealed this kinase to be composed of a large catalytic subunit, termed DNA-PKcs, and a regulatory component termed Ku. DNA-PK has been shown to be a crucial component of both the DNA double-strand break (DSB) repair machinery and the V(D)J recombination apparatus. In addition, recent work has implicated DNA-PK components in a variety of other processes, including the modulation of chromatin structure and telomere maintenance (Smith, G. C. M. and Jackson, S. P., *Genes and Dev.*, 13, 916-934 (1999)).

DNA DSBs are regarded as the most lethal lesion a cell can encounter. To combat the serious threats posed by DNA DSBs, eukaryotic cells have evolved several mechanisms to mediate their repair. In higher eukaryotes, the predominant of these mechanisms is DNA non-homologous end-joining (NHEJ), also known as illegitimate recombination. DNA-PK plays a key role in this pathway. Increased DNA-PK activity has been demonstrated both in vitro and in vivo and correlates with the resistance of tumour cells to IR and bifunctional alkylating agents (Muller C., et al., *Blood*, 92, 2213-2219 (1998), Sirzen F., et al., *Eur. J. Cancer*, 35, 111-116 (1999)). Therefore, increased DNA-PK activity has been proposed as a cellular and tumour resistance mechanism. Hence, inhibition of DNA-PK with a small molecule inhibitor may prove efficacious in tumours where over-expression is regarded as a resistance mechanism.

It also has been previously found that the PI 3-kinase inhibitor LY294002:

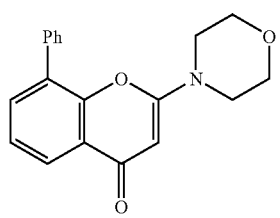

is able to inhibit DNA-PK function in vitro (Izzard, R. A., et al., *Cancer Res.*, 59, 2581-2586 (1999)). The $IC_{50}$ (concentration at which 50% of enzyme activity is lost) for LY294002 towards DNA-PK is, at ~1 µM, the same as that for PI 3-kinase. Furthermore it has been shown that LY294002 is also able to weakly sensitise cells to the effects of IR (Rosenzweig, K. E., et al., *Clin. Cancer Res.*, 3, 1149-1156 (1999)).

WO 03/024949 describes a number of classes of compounds useful as DNA-PK inhibitors, including 2-amino-chromen-4-ones of the general structure:

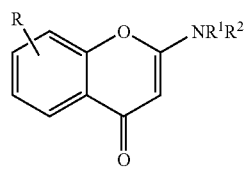

of which:

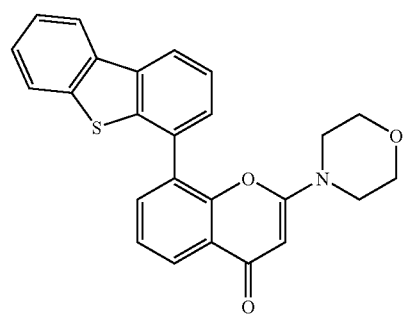

was one example. This compound exhibited an $IC_{50}$ of 10-12 nM and an SER of 1.3 (100 nM) (see below for methods).

Other examples of DNA-PK inhibitors include 1(2-hydroxy-4-morpholin-4-yl-phenyl)-ethanone (Kashishian, A., et al., *Mol. Cancer Ther*, 2, 1257-1264 (2003)):

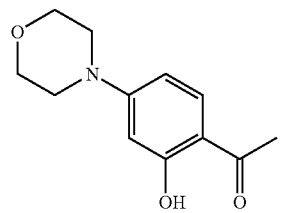

and SU11752 (Ismail, I. H., et al., *Oncogene*, 23, 873-882 (2004))

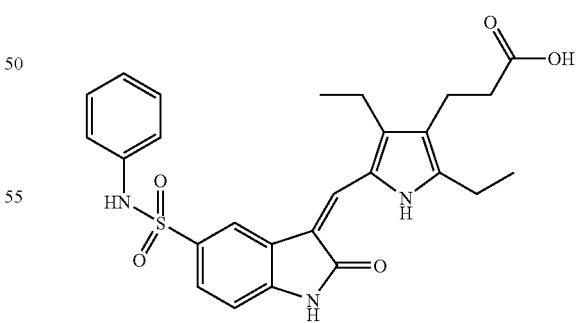

Given the involvement of DNA-PK in DNA repair processes, and that small molecule inhibitors have been shown to radio- and chemo-sensitise mammalian cells in culture, an application of specific DNA-PK inhibitory drugs would be to act as agents that will enhance the efficacy of both cancer chemotherapy and radiotherapy. DNA-PK inhibitors may also prove useful in the treatment of retroviral mediated diseases. For example it has been demonstrated that loss of DNA-PK activity severely represses the process of retroviral integration (Daniel R, et al., *Science*, 284, 644-7 (1999)).

The present inventors have now discovered further compounds which exhibit similar or improved levels of DNA-PK inhibition, whilst possessing other useful properties for use as active pharmaceuticals, in particular improved solubility and cellular efficacy.

Accordingly, the first aspect of the invention provides a compound of formula I:

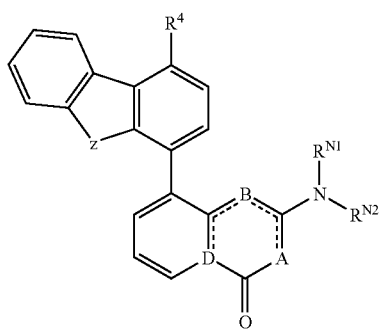

and isomers, salts, solvates, chemically protected forms, and prodrugs thereof, wherein: A, B and D are respectively selected from the group consisting of:

(i) CH, NH, C;

(ii) CH, N, N; and (iii) CH, O, C;

the dotted lines represent two double bonds in the appropriate locations;

$R^{N1}$ and $R^{N2}$ are independently selected from hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms;

if A, B, D are selected from groups (i), (ii) above, Z is selected from the group consisting of S, O, C(=O), $CH_2$ and NH; if A, B, D represent group (iii), Z is selected from the group consisting of O, C(=O), $CH_2$ and NH;

$R^4$ is selected from the group of H, OH, $NO_2$, $NH_2$ and Q-Y—X where

Q is —NH—C(=O)— or —O—;

Y is an optionally substituted $C_{1-5}$ alkylene group;

X is selected from $SR^{S1}$ or $NR^{N3}R^{N4}$, wherein, $R^{S1}$, or $R^{N3}$ and $R^{N4}$ are independently selected from hydrogen, optionally substituted $C_{1-7}$ alkyl, $C_{5-20}$ aryl, or $C_{3-20}$ heterocyclyl groups, or $R^{N3}$ and $R^{N4}$ may together form, along with the nitrogen atom to which they are attached, an optionally substituted heterocyclic ring having from 4 to 8 ring atoms;

if Q is —O—, X may additionally be selected from —C(=O)—$NR^{N5}R^{N6}$, wherein $R^{N5}$ and $R^{N6}$ are independently selected from hydrogen, optionally substituted $C_{1-7}$ alkyl, $C_{5-20}$ aryl, or $C_{3-20}$ heterocyclyl groups, or $R^{N5}$ and $R^{N6}$ may together form, along with the nitrogen atom to which they are attached, an optionally substituted heterocyclic ring having from 4 to 8 ring atoms and if Q is —NH—C(=O)—, —Y—X may additionally selected from $C_{1-7}$ alkyl;

with the proviso that if A, B, D represent group (iii) and $R^{N1}$ and $R^{N2}$ together with the carbon atom to which they are bound form a morpholino group, $R^4$ cannot be H.

The options for A, B and D result in compounds of the following formulae:

| Formula | A | B | D | Structure |
|---------|---|---|---|-----------|
| Ia | CH | NH | C | 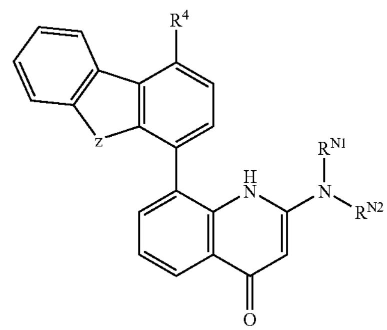 |
| Ib | CH | N | N | 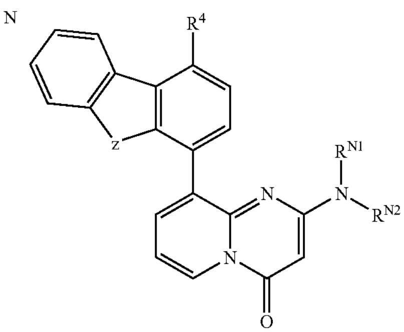 |
| Ic | CH | O | C | 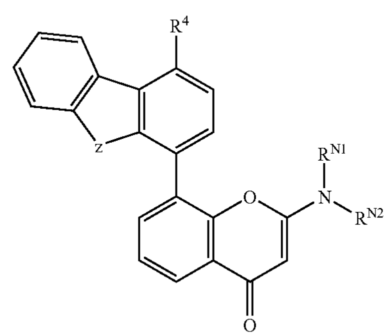 |

A second aspect of the invention provides a composition comprising a compound of the first aspect and a pharmaceutically acceptable carrier or diluent.

A third aspect of the invention provides a compound of the first aspect for use in a method of therapy.

A fourth aspect of the invention provides for the use of a compound of the first aspect in the preparation of a medicament for treating a disease ameliorated by the inhibition of DNA-PK.

It is preferred that the medicament of the fourth aspect selectivity inhibits the activity of DNA-PK compared to PI 3-kinase and/or ATM. Selectivity is an important issue as inhibition of other PI 3-kinase family members may lead to unwanted side-effects associated with the loss of function of those enzymes.

In particular, the compounds may be used in the preparation of a medicament for:

(a) use as an adjunct in cancer therapy or for potentiating tumour cells for treatment with ionising radiation or chemotherapeutic agents; or (b) the treatment of retroviral mediated diseases.

A further aspect of the invention provides an active compound as described herein for use in a method of treatment of the human or animal body, preferably in the form of a pharmaceutical composition.

Another aspect of the invention provides a method of inhibiting DNA-PK in vitro or in vivo, comprising contacting a cell with an effective amount of an active compound as described herein.

DEFINITIONS $C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring.

Preferably, each ring has from 3 to 7 ring atoms, of which from 1 to 4 are ring heteroatoms. Ring heteroatoms may preferably be selected from the group consisting of O, N, S and P. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$ heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heterocyclic groups (some of which are $C_{5-20}$ heteroaryl groups) which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl and $C_{5-20}$ aryl groups whether alone or part of another substituent, may themselves optionally be substituted with one or more groups selected from themselves and the additional substituents listed below.

Halo: —F, —Cl, —Br, and —I.
Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. $R^1$ and $R^2$ may together form a cyclic structure, as in, for example, succinimidyl, maleimidyl and phthalimidyl:

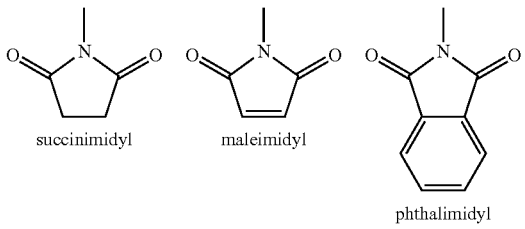

succinimidyl    maleimidyl    phthalimidyl

Acylureido: —N($R^1$)C(O)N$R^2$C(O)$R^3$ wherein $R^1$ and $R^2$ are independently ureido substituents, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. $R^3$ is an acyl group as defined for acyl groups. Examples of acylureido groups include, but are not limited to, —NHCONHC(O)H, —NHCONMeC(O)H, —NHCONEtC(O)H, —NHCONMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: —NR$^1$—C(O)—OR$^2$ wherein $R^1$ is an amino substituent as defined for amino groups and $R^2$ is an ester group as defined for ester groups. Examples of carbamate groups include, but are not limited to, —NH—C(O)—O-Me, —NMe—C(O)—O-Me, —NH—C(O)—O-Et, —NMe-C(O)—O-t-butyl, and —NH—C(O)—O-Ph.

Thioamido (thiocarbamyl): —C(=S)N$R^1R^2$, wherein $R^1$ and $R^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom,

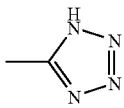

Amino: —NR$^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)NH$_2$.

Carbazoyl (hydrazinocarbonyl): —C(O)—NN—R$^1$ wherein $R^1$ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH$_2$-Ph.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein $R^1$ is an amino substituent, as defined for amino groups. Examples of sulfamino groups include, but are not limited to, —NHS(=O)$_2$OH and —N(CH$_3$)S(=O)$_2$OH.

Sulfinamino: —NR$^1$S(=O)R, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams—in these groups one of R$^1$ and R is a $C_{5-20}$ aryl group, preferably phenyl, whilst the other of R$^1$ and R is a bidentate group which links to the $C_{5-20}$ aryl group, such as a bidentate group derived from a $C_{1-7}$ alkyl group. Examples of such groups include, but are not limited to:

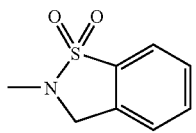 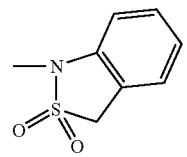

2,3-dihydro-tenzo[d]isothiazole-1,1-dioxide-2-yl
1,3-dihydro-benzo[c]isothiazole-2,2-dioxide-1-yl

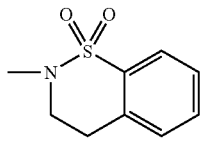

3,4-dihydro-2H-benzo[e][1,2]thiazine-1,1-dioxide-2-yl

Phosphoramidite: —OP(OR$^1$)—NR$^2$$_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$ alkoxy group), for example, cyclohexylmethoxy, a $C_{3-20}$ heterocyclyl group (also referred to as a $C_{5-20}$ aryl-$C_{1-7}$ alkoxy group), for example phthalimidoethoxy, or a $C_{5-20}$ aryl group (also referred to as a $C_{5-20}$aryl-$C_{1-7}$alkoxy group), for example, benzyloxy.

$C_{1-5}$ Alkylene: The term "$C_{1-5}$ alkylene", as used herein, pertains to a bidentate moiety obtained by removing two hydrogen atoms, either both from the same carbon atom, or one from each of two different carbon atoms, of an aliphatic linear hydrocarbon compound having from 1 to 5 carbon atoms (unless otherwise specified), which may be saturated, partially unsaturated, or fully unsaturated. Thus, the term "alkylene" includes the sub-classes alkenylene, alkynylene, etc., discussed below.

Examples of saturated $C_{1-5}$ alkylene groups include, but are not limited to, —(CH$_2$)$_n$— where n is an integer from 1 to 5, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of partially unsaturated $C_{1-5}$ alkylene groups include, but is not limited to, —CH=CH— (vinylene), —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH— and —CH=CH—CH=CH—CH$_2$—.

The substituent groups listed above may be substituents on an alkylene group.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

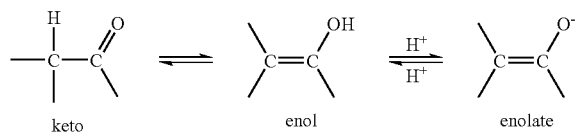

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selective Inhibition

'Selective inhibition' means the inhibition of one enzyme to a greater extent than the inhibition of one or more other enzymes. This selectivity is measurable by comparing the concentration of a compound required to inhibit 50% of the activity ($IC_{50}$) of one enzyme against the concentration of the same compound required to inhibit 50% of the activity ($IC_{50}$) of the other enzyme (see below). The result is expressed as a ratio. If the ratio is greater than 1, then the compound tested exhibits some selectivity in its inhibitory action.

The compounds of the present invention preferably exhibit a selectivity of greater than 3, 10, 20 or 50 against DNA-PK over PI 3-kinase.

The compounds of the present invention preferably exhibit a selectivity of greater than 5, 10, 50 or 100 against DNA-PK over ATM.

It is preferred that the $IC_{50}$ values used to assess selectivity are determined using the methods described in WO 03/024949, which is herein incorporated by reference.

Further Preferences $R^4$

It is preferred that $R^4$ is Q-Y—X.

When Q is —NH—C(=O)—, X is preferably $NR^{N3}R^{N4}$. It is further preferred that Y is an optionally substituted $C_{1-3}$ alkylene group, more preferably an optionally substituted $C_{1-2}$ alkylene group and most preferably a $C_{1-2}$ alkylene group.

When Q is —O— and X is $NR^{N3}R^{N4}$, then Y is preferably an optionally substituted $C_{1-3}$ alkylene group, more preferably an optionally substituted $C_{1-2}$ alkylene group and most preferably a $C_{1-2}$ alkylene group.

In some embodiments, $R^{N3}$ and $R^{N4}$ are preferably independently selected from H and optionally substituted $C_{1-7}$ alkyl, more preferably H and optionally substituted $C_{1-4}$ alkyl and most preferably H and optionally substituted $C_{1-3}$ alkyl (e.g. methyl, ethyl, iso-propyl). Preferred optional substitutents include, but are not limited to, hydroxy, methoxy, —$NH_2$, optionally substituted $C_6$-aryl and optionally substituted $C_{5-6}$ heterocyclyl.

In other embodiments, $R^{N3}$ and $R^{N4}$ form, together with the nitrogen atom to which they are attached, an optionally substituted nitrogen containing heterocylic ring having from 4 to 8 ring atoms. Preferably, the heterocyclic ring has 5 to 7 ring atoms. Examples of preferred groups include, morpholino, piperidinyl, piperazinyl, homopiperazinyl and tetrahydropyrrolo, with piperazinyl being particularly preferred. These groups may be substituted, and a particularly preferred group is optionally substituted piperazinyl, where the substituent is preferably on the 4-nitrogen atom. Preferred N-substituents include optionally substituted $C_{1-4}$ alkyl, optionally substituted $C_6$ aryl and acyl (with a $C_{1-4}$ alkyl group as the acyl substituent).

Z

Z is preferably selected from S and O, where appropriate, and is more preferably S.

$R^{N5}$ and $R^{N6}$

The preferences for $R^{N5}$ and $R^{N6}$ may be the same as for $R^{N3}$ and $R^{N4}$ expressed above.

$R^{N1}$ and $R^{N2}$

In compounds of formula I, when $R^{N1}$ and $R^{N2}$ form, along with the nitrogen atom to which they are attached, a heterocyclic ring having from 4 to 8 atoms, this may form part of a $C_{4-20}$ heterocyclyl group defined above (except with a minimum of 4 ring atoms), which must contain at least one nitrogen ring atom. It is preferred that $R^{N1}$ and $R^{N2}$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

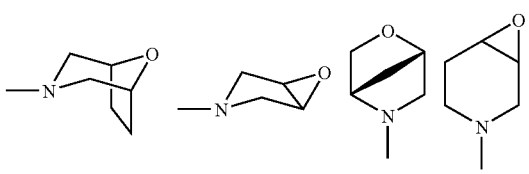

These are named 8-oxa-3-aza-bicyclo[3.2.1]oct-3-yl, 6-oxa-3-aza-bicyclo[3.1.0]hex-3-yl, 2-oxa-5-aza-bicyclo[2.2.1]hept-5-yl, and 7-oxa-3-aza-bicyclo[4.1.0]hept-3-yl, respectively.

General Synthesis Methods

Compounds of formula I, where $R^4$ is Q-Y—X and Q is —NH—C(=O)— can be represented as Formula 1:

Formula 1

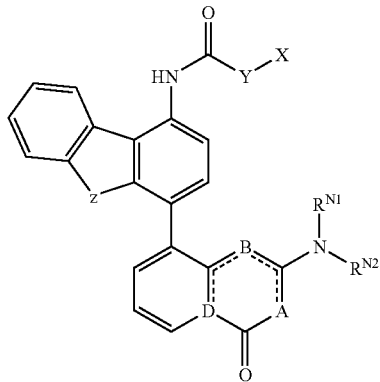

These compounds, where —Y—X is not $C_{1-7}$ alkyl, can be made from compounds of formula 2:

Formula 2

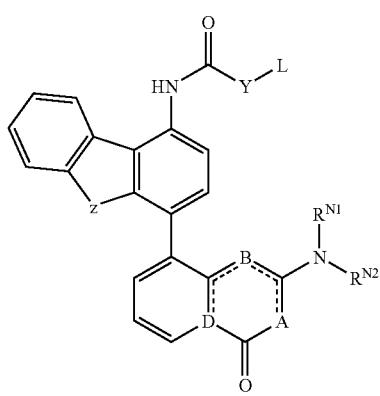

wherein L is a leaving group such as chloro or bromo, by reacting with the appropriate amine or thiol. This reaction can be carried at room temperature, or may be heated, if necessary.

Compounds of formula 2 can be synthesised by the reaction of a compound of formula 3:

Formula 3

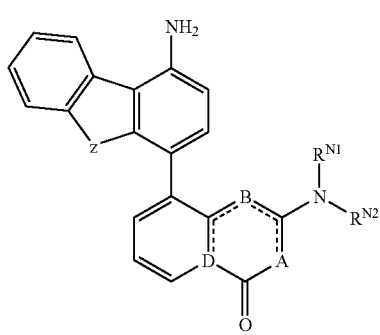

with a compound of formula 4:

Formula 4

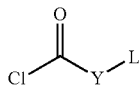

in the presence of an organic base, for example, triethylamine.

Compounds of formula 1 where —Y—X is $C_{1-7}$ alkyl can be synthesised by the reaction of a compound of formula 3 with a compound of formula 4a:

Formula 4a

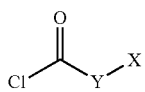

in the presence of an organic base, for example, triethylamine.

The compounds of formula 3 may be synthesised by reducing a compound of formula 5:

Formula 5

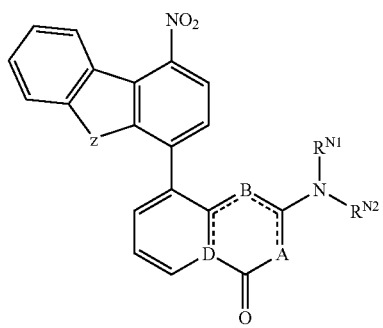

using an appropriate reducing agent, for example, zinc in acetic acid.

Compounds of formula 5 can be synthesised by the Suzuki-Miyaura coupling of compounds of formula 6 and 7:

Formula 6

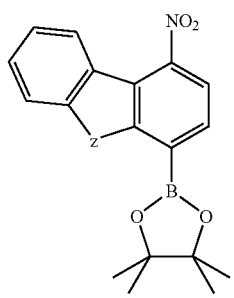

Formula 7

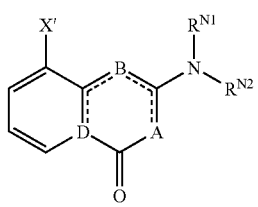

where X' is a group such as bromo or OTf. The coupling moieties may be reversed.

Compounds of formula 7 may be synthesised as follows.
Compounds of formula 7a:

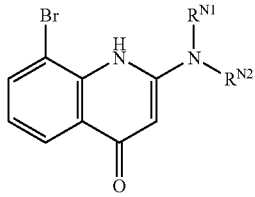

Formula 7a may be synthesised from compounds of formula 8a:

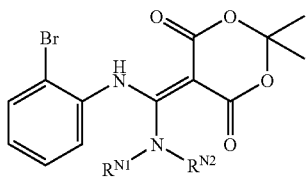

Formula 8a by cyclocondensation via pyrolysis with decarboxylation.

The compounds of formula 8a may be synthesised from a compound of formula 9a:

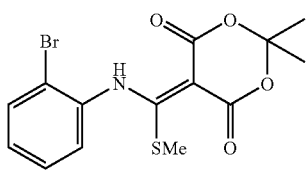

Formula 9a by reaction with the appropriate amine of formula $HNR^{N1}R^{N2}$, in an appropriate solvent.

The compound of formula 9a can be synthesised from a compound of formula 10a:

Formula 10a by reaction with a Meldrum's acid derivative of formula 11a:

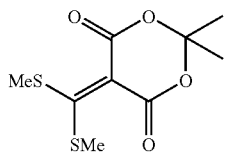

Formula 11a in an appropriate solvent.

Compounds of formula 7b:

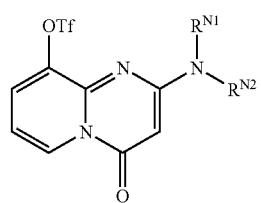

Formula 7b may be synthesised by reacting a compound of formula 8b:

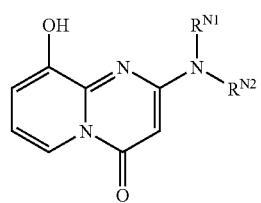

Formula 8b with triflic anhydride, in a solvent such as DCM, in the presence of a base, such as triethylamine.

Compounds of formula 8b may be synthesised from a compound of formula 9b:

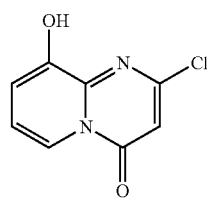

Formula 9b by nucleophilic substitution of the chloride by an amine of formula $HNR^1R^2$.

The compound of formula 9b can be synthesised from a compound of formula 10b:

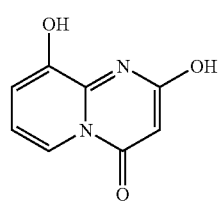

Formula 10b by chlorination using a chlorinating agent, e.g. $POCl_3$. The compound of formula 10b may be synthesised from a compound of formula 11b:

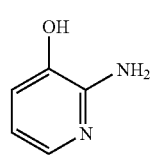

Formula 11b by reaction with diethyl malonate, or an equivalent thereof.

Compounds of formula 7c:

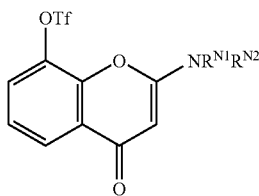
Formula 7c

Routes to compounds of formula 7c are described in WO 03/024949 (Synthesis Route 6).

Compounds of formula I, where $R^4$ is Q-Y—X, Q is —O— and X is selected from $SR^{S1}$ or $NR^{N3}R^{N4}$ can be represented as Formula 13:

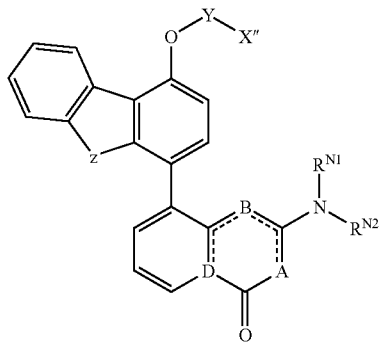
Formula 13 wherein X" represents $SR^{S1}$ or $NR^{N3}R^{N4}$. These compounds may be synthesised from compounds of formula 14:

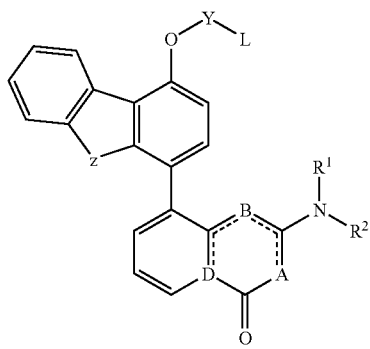
Formula 14 wherein L is a leaving group, for example chloro or bromo, by reacting with the appropriate amine or thiol. This reaction can be carried at room temperature, or may be heated, if necessary.

Compounds of formula 14 may be synthesised by the reaction of a compound of formula 15:

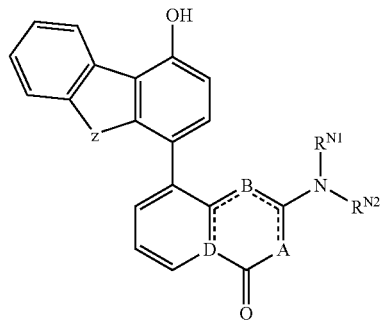
Formula 15 with a compound of formula 16:

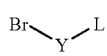
Formula 16 wherein, if Y is non-symmetrical, it is preferred that L is not Br, in the presence of, for example, potassium carbonate.

Compounds of formula 15 can be synthesised from compounds of formula 3 using a diazotisation-hydrolysis procedure. This first converts the amino group into the diazonium fluoroborate salt, for example, using $HBF_4$ and butyl nitrite, which is then hydrolysed using, for example, aqueous copper (I) oxide-copper (II) nitrate.

Compounds of formula I, where Q is —O— and X is —C(=O)—$NR^{N5}R^{N6}$ can be represented as Formula 17:

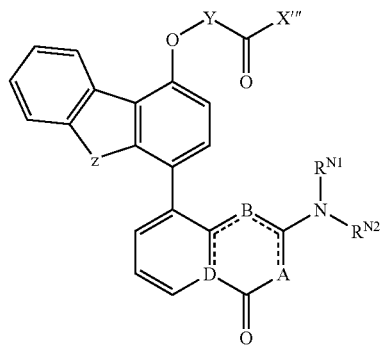
Formula 17 wherein X''' represents $NR^{N5}R^{N6}$. These compounds may be synthesised from compounds of formula 18:

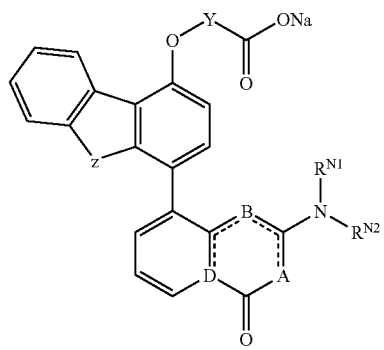
Formula 18 by reaction with the appropriate amine in the presence of HBTU and HOBT.

Compounds of formula 18 may be made from compounds of formula 19:

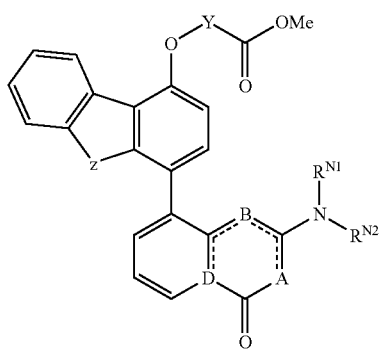

Formula 19 by reaction with sodium hydroxide in methanol. The compounds of formula 19 may be synthesised from compounds of formula 15 by reaction with a compound of formula 20:

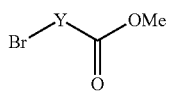

Formula 20 in the presence of, for example, potassium carbonate.

Compounds of the present invention where $R^4$ is H may be made by the coupling of an appropriate boronic acid to a compound of formula 7, in an analagous way to that described above.

Use of Compounds of the Invention

The present invention provides active compounds, specifically, active 8-aryl-2-amin-4-yl-quinolin-4-ones, pyridopyrimidine-4-ones, and chromen-4-ones.

The term "active", as used herein, pertains to compounds which are capable of inhibiting DNA-PK activity, and specifically includes both compounds with intrinsic activity (drugs) as well as prodrugs of such compounds, which prodrugs may themselves exhibit little or no intrinsic activity.

One assay which may be used in order to assess the DNA-PK inhibition offered by a particular compound is described in the examples below.

The present invention further provides a method of inhibiting DNA-PK inhibition in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit DNA-PK activity as well as methods of methods of inhibiting DNA-PK activity comprising contacting a cell with an effective amount of an active compound, whether in vitro or in vivo.

Active compounds may also be used as cell culture additives to inhibit DNA-PK, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

The term "adjunct" as used herein relates to the use of active compounds in conjunction with known therapeutic means. Such means include cytotoxic regimes of drugs and/or ionising radiation as used in the treatment of different cancer types. Examples of adjunct anti-cancer agents that could be combined with compounds from the invention include, but are not limited to, the following: alkylating agents: nitrogen mustards, mechlorethamine, cyclophosphamide, ifosfamide, melphalan, chlorambucil: Nitrosoureas: carmustine (BCNU), lomustine (CCNU), semustine (methyl-CCNU), ethylenimine/methylmelamine, thriethylenemelamine (TEM), triethylene thiophosphoramide (thiotepa), hexamethylmelamine (HMM, altretamine): Alkyl sufonates; busulfan; Triazines, dacarbazine (DTIC): Antimetabolites; folic acid analogs, methotrexate, trimetrexate, pyrimidine analogs, 5-fluorouracil, fluorodeoxyuridine, gemcitabine, cytosine arabinoside (AraC, cytarabine), 5-azacytidine, 2,2'-difluorodeoxycytidine: Purine analogs; 6-mercaptopurine, 6-thioguanine, azathioprine, 2'-deoxycoformycin (pentostatin, erythrohydroxynonyladenine (EHNA), fludarabine phosphate, 2-Chlorodeoxyadenosine (cladribine, 2-CdA): Topoisomerase I inhibitors; camptothecin, topotecan, irinotecan, rubitecan: Natural products; antimitotic drugs, paclitaxel, vinca alkaloids, vinblastine (VLB), vincristine, vinorelbine, Taxotere™ (docetaxel), estramustine, estramustine phosphate; epipodophylotoxins, etoposide, teniposide: Antibiotics; actimomycin D, daunomycin (rubidomycin), doxorubicin (adriamycin), mitoxantrone, idarubicin, bleomycins, plicamycin (mithramycin), mitomycin C, dactinomycin: Enzymes; L-asparaginase, RNAse A: Biological response modifiers; interferon-alpha, IL-2, G-CSF, GM-CSF: Differentiation Agents; retinoic acid derivatives: Radiosensitizers, metronidazole, misonidazole, desmethylmisonidazole, pimonidazole, etanidazole, nimorazole, RSU 1069, EO9, RB 6145, SR4233, nicotinamide, 5-bromodeozyuridine, 5-iododeoxyuridine, bromodeoxycytidine: Platinium coordination complexes; cisplatin, carboplatin: Anthracenedione; mitoxantrone, AQ4N Substituted urea, hydroxyurea; Methylhydrazine derivatives, N-methylhydrazine (MIH), procarbazine; Adrenocortical suppressant, mitotane (o.p'-DDD), aminoglutethimide: Cytokines; interferon (α, β, γ), interleukin; Hormones and antagonists; adrenocorticosteroids/antagonists, prednisone and equivalents, dexamethasone, aminoglutethimide; Progestins, hydroxyprogesterone caproate, medroxyprogesterone acetate, megestrol acetate; Estrogens, diethylstilbestrol, ethynyl estradiol/equivalents; Antiestrogen, tamoxifen; Androgens, testosterone propionate, fluoxymesterone/equivalents; Antiandrogens, flutamide, gonadotropin-releasing hormone analogs, leuprolide; Nonsteroidal antiandrogens, flutamide; EGFR inhibitors, VEGF inhibitors; Proteasome inhibitors.

Cancer

The present invention provides active compounds which are anticancer agents or adjuncts for treating cancer. One of ordinary skill in the art is readily able to determine whether or not a candidate compound treats a cancerous condition for any particular cell type, either alone or in combination.

Examples of cancers include, but are not limited to, lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma and leukemias. Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (Cl 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (AvastinT) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), trifluoroacetic acid (TFA), dimethylformamide (DMF), tetrahydrofuran (THF), and dimethylsulfoxide (DMSO).

General Experimental Details

Chemicals were purchased from the Aldrich Chemical Company, Lancaster Synthesis Ltd and Acros Organics (Fisher Scientific UK Ltd). THF was freshly distilled from sodium/benzophenone. Methanol and ethanol were distilled from magnesium/iodine. DCM was dried by distillation over phosphorus pentoxide. Acetone was dried by distillation over calcium hydride. All solvents not used immediately were stored over molecular sieves (4 Å, 3-5 mm beads), under nitrogen. Anhydrous DMF was obtained from Aldrich in SureSeal™ bottles. Triethylamine was dried by distillation over calcium hydride and stored over potassium hydroxide, under nitrogen.

Thin layer chromatography (TLC), was performed using Merck silica gel $60F_{254}$ pre-coated on aluminium sheets which were subsequently dried and visualised using either short wave (254 nm) ultraviolet light or by treatment with either ninhydrin or sulphuric acid then vanillin. 'Flash' column chromatography was carried out at medium pressure using Davisil silica gel (40-63 μm).

Melting points were determined using a Stuart Scientific SMP3 apparatus and are uncorrected. $^1H$ and $^{13}C$ nuclear magnetic resonance (NMR) spectra were obtained using a Bruker Spectrospin AC 300E spectrometer ($^1H$ 300 MHz or $^{13}C$ 75 MHz) or a Bruker Spectrospin AC 500E spectrometer ($^1H$ 500 MHz or $^{13}C$ 125 MHz). Chemical shifts are reported in parts per million (δ) downfield of teramethylsulfone using residual solvent peaks as internal standards. Multiplicities are indicated by s (singlet), d (doublet), t (triplet), q (quartet), m (multiplet), br (broad) or combinations thereof. LC/MS spectra were obtained using a Micromass Platform instrument running in positive or negative ion electrospray mode. Separation was achieved using a C18 column (50×4.6 mm; Supelco Discovery or Waters Symmetry) and a 15 minute gradient elution of 0.05% formic acid and methanol (10-90%). IR spectra were recorded on a Bio-Rad FTS 3000MX diamond ATR as a neat sample.

Synthesis of Key Intermediates (i) Trifluoro-methanesulfonic acid 1-nitro-dibenzothiophen-4-yl ester (6)

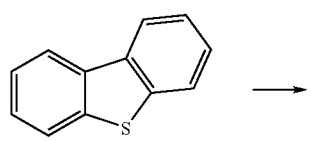

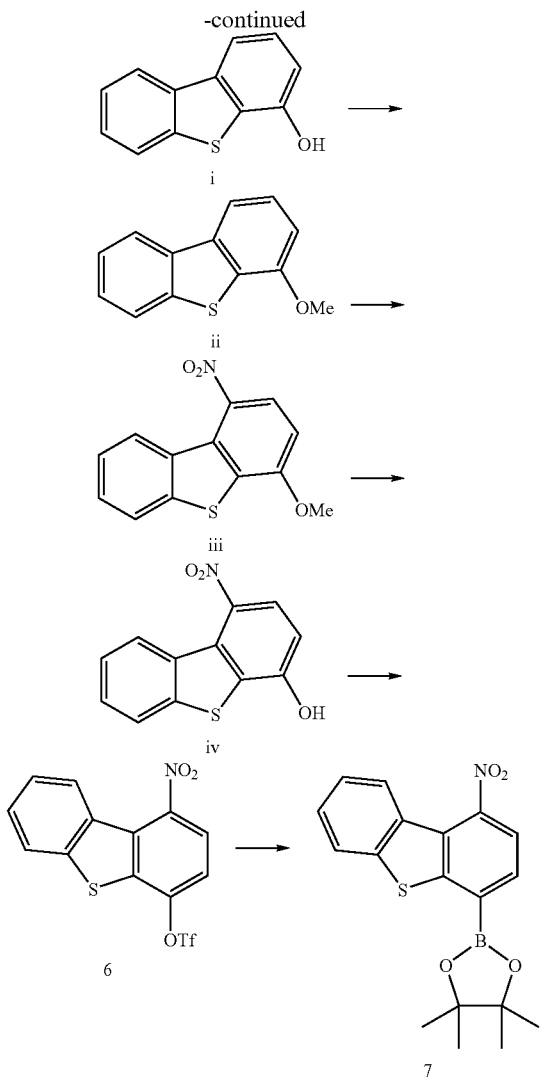

(a) Dibenzothiophen-4-ol (i)

To a cooled (−78° C.) solution of dibenzothiophene (20.8 g, 113 mmol) in anhydrous THF (400 ml) was added tert-butyl lithium (1.7 M in pentane; 100 ml, 170 mmol). The reaction mixture was stirred at −78° C. for 1 hour and then allowed to warm to room temperature and stirred like this for 16 hours. The mixture was then cooled to 0° C. and ethylmagnesium bromide (1M in THF; 170 ml, 170 mmol) added to the amber reaction mixture in a slow stream via cannula. The reaction was again allowed to room temperature whereupon it was stirred like this for 30 minutes. A reflux condenser was attached to the reaction vessel before oxygen was bubbled through the solution for 40 minutes. The mixture was then stirred for a further 1 hour before carefully pouring onto crushed ice and acidifying to pH 3 with concentrated HCl. The mixture was then extracted using ethyl acetate (3×80 ml). The organic extracts were then treated with 3M sodium hydroxide solution until pH 10 was attained. The basic, aqueous layer was separated, acidified to pH 3 with 2M HCl which caused an oily solid to precipitate. This was dissolved in diethylether (150 ml), dried using $MgSO_4$, filtered and concentrated in vacuo and then recrystallised from ethanol:water (1:1) (250 ml) to give a buff coloured solid that corresponded to the title compound (21.6 g, 96%) and required no further purification. m/z (LC-MS, ESP), RT=3.64 min, (M+H)= 201.1.

(b) 4-Methoxy-dibenzothiophene (ii)

To a solution of dibenzothiophen-4-ol (i)(14.2 g, 71.0 mmol) in acetone (500 ml) was added powdered potassium carbonate (14.72 g, 106.5 mmol) and methyl iodide (4.43 ml, 71 mmol). The mixture was heated to reflux and stirred like this for 16 hours. The mixture was then cooled and filtered through a Celite™ pad. The resulting filtrant was concentrated in vacuo to give an oily residue that was diluted in dichloromethane (100 ml) and washed with 1M NaOH and saturated brine solution. The organic layer was dried using $MgSO_4$, filtered and concentrated in vacuo to give a buff coloured solid that corresponded to the title compound and was used without any further purification. (15.2 g, 100%) m/z (LC-MS, ESP), RT=4.22 min, (M+H)=215.1.

(c) 4-Methoxy-1-nitro-dibenzothiophene (iii)

4-Methoxy-dibenzothiophene (ii)(4.3 g, 20.0 mmol) was dissolved in glacial acetic acid (60 ml) and to this solution was added fuming nitric acid (3.37 ml) in a dropwise fashion ensuring that the temperature of the mixture did not rise above 25° C. The yellow suspension was stirred for a further 45 minutes before being poured carefully into water (200 ml) and stirred for 15 minutes. The yellow solid was removed by filtration and washed thoroughly with copious amounts of water and then hexanes. The residue thus obtained was then dried in a vacuum oven to give the title compound as a yellow solid which was used without any further purification. (5.19 g, 97%) m/z (LC-MS, ESP), RT=4.15 min, (M+H)=260.1.

(d) 1-Nitro-dibenzothiophen-4-ol (iv)

Solid pyridine hydrochloride (1 kg, 8.7 mol) was added to 4-methoxy-1-nitro-dibenzothiophene (iii)(35.44 g, 187 mmol) and the reaction mixed well before heating to 165° C. with continuous stirring. The mixture was maintained like this for 8 hrs, cooled, diluted with water (500 ml) and extracted into dichloromethane (3×200 ml). 3M sodium hydroxide solution was added to the organic extract until a dark solid precipitated from the solution. The filtrate was removed and the liquor acidified to pH1 using concentrated HCl. The resulting bright yellow solid that formed on acidification was then removed by filtration, washed with water and dried to give the title compound that was suitably pure to be used without any further purification. (35.44 g, 77%) m/z (LC-MS, ESP), RT=3.69 min, (M+H)=246.2, (M−H)=244.1.

(e) Trifluoro-methanesulfonic acid 1-nitro-dibenzothiophen-4-yl ester (6)

To a cooled (−5° C.) suspension of 1-nitro-dibenzothiophen-4-ol (iv)(5.37 g, 22.0 mmol) in dichloromethane (75 ml) was added triethylamine (9.20 ml, 66.00 mmol) which caused the suspension to solublise completely. To this mixture was then added trifluoromethanesulfonic anhydride (5.85 ml, 33.00 mmol) in a dropwise fashion via syringe. The mixture was stirred at this temperature for 1 hour and then poured onto crushed ice. The ice was allowed to melt and the mixture extracted using $CH_2Cl_2$ (3×20 ml). The combined organic layers were then dried ($MgSO_4$), filtered and concentrated in vacuo to give a mild amber oil that was eluted though a pad of silica (neat $CH_2Cl_2$) to give the title compound in a suitably pure form to be used without any further purification. (8.30 g, 99%) %) m/z (LC-MS, ESP), RT=4.40 min, did not ionize.

(f) 1-Nitro-4-(4,4,5,5-tetramethyl-1,3,2-dioxaborolan-2-yl)dibenzothiophene (7)

A clean, dry flask was charged with trifluoro-methanesulfonic acid 1-nitro-dibenzothiophen-4-yl ester (6) (250 mg, 0.66 mmol), bis(pinacolato)diboron (185 mg, 0.73 mmol), potassium acetate (390 mg, 3.98 mmol), $PdCl_2$(dppf) (27 mg, 0.033 mmol), and dppf (19 mg, 0.033 mmol) under argon. The flask was evacuated under vacuum and flushed with argon three times. Dioxane (20 ml) was added and the reaction mixture was stirred at 90° C. for 12 hours. The reaction mixture was diluted with DCM (100 ml) and organic layer was washed successively with water (3×30 ml), brine (1×30 ml), dried ($Na_2SO_4$) and the solvent was evaporated in vacuo to furnish the nitroboronate ester (7) which was used without further purification.

(ii) 1-Nitro-4-(4,4,5,5-tetramethyl-1,3,2-dioxaborolan-2-yl)dibenzofuran (12)

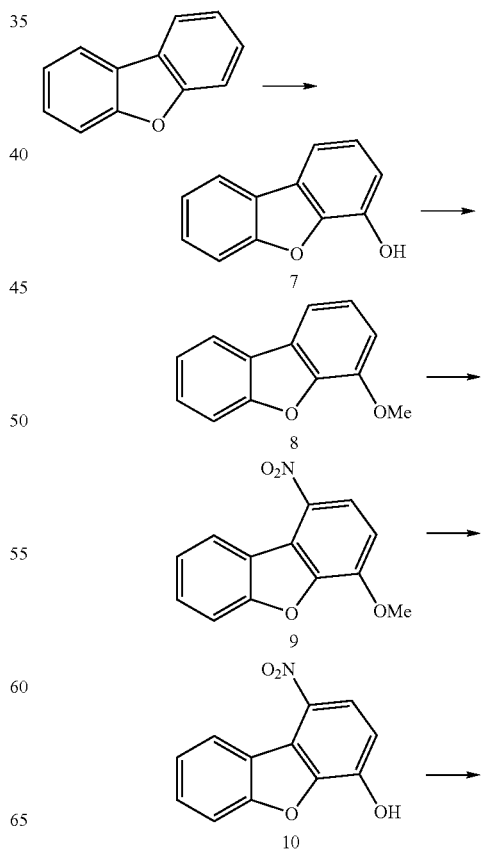

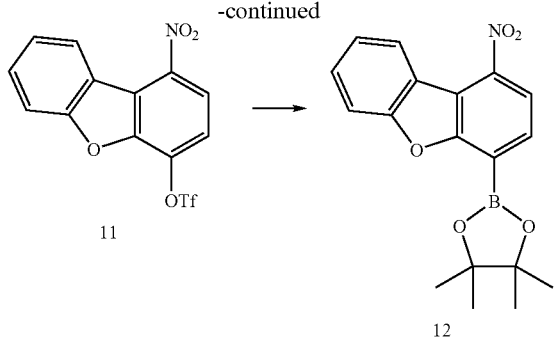

(a) Dibenzofuran-4-ol (7)

n-BuLi (120 mL, 300 mmol) was added to a solution of dibenzofuran (27.4 g, 163 mmol) in dry THF at −78° C. The reaction was slowly heated at 40° C. and stirred for 18 h. The reaction was then cooled at −5° C. and MeMgBr (100 mL, 300 mmol) was added dropwise. After the addition was completed, the reaction was stirred at room temperature for 1 hour. A reflux condenser with bubbler was fitted, and oxygen was bubbled through the reaction for 4 h, during which time the reaction was slowly heated at 40° C. Continuing bubbling oxygen did not increase the progress of the reaction. The reaction was quenched by carefully pouring the reaction mixture into ice. The pH was adjusted to 3 via the addition of concentrated HCl, and the product was extracted into DCM. The residue was purified by flash chromatography using DCM/EP (6:4) as eluant. After evaporation, some unreacted dibenzofuran was also isolated (13 g, 47%). The product (10.9 g, 59 mmol, 36%) was obtained as a white solid: $R_f$=0.18 (DCM-EP 6:4); mp: 102° C.; $\lambda_{max}$ (EtOH)/nm 234; IR (cm$^{-1}$) 3258, 3049, 1635, 1603, 1477, 1436, 1347, 1309, 1245, 1189, 1158; $^1$H NMR, (300 MHz, CDCl$_3$) δ 5.40 (1H, s, OH), 7.05 (1H, d, $J_{H2\text{-}H3}$=8 Hz, H-3), 7.27 (1H, d, J=8 Hz), 7.38 (1H, t, J=7 Hz), 7.47-7.56 (2H, m), 7.61 (1H, d, J=8 Hz), 7.97 (1H, d, J=8 Hz); $^{13}$C NMR, (75 MHz, CDCl$_3$) δ 111.84, 112.79, 113.95, 121.00, 122.97, 123.72, 124.63 (Cq), 125.90 (Cq), 127.26, 141.35 (Cq), 144.31 (Cq), 156.04 (Cq); MS (EI) m/z 184.0 M$^+$; HRMS calcd for $C_{12}H_8O_2$ [M+H]$^+$ 184.0519, found 184.0517.

(b) 4-Methoxy-dibenzofuran (8)

Potassium carbonate (1.4 g, 10.11 mmol) and methyl iodide (0.42 mL, 6.74 mmol) were added to a solution of dibenzofuran-4-ol (1.24 g, 6.74 mmol) in acetone (65 mL). The reaction was heated at reflux and stirred for 18 h. Upon cooling, the reaction mixture was successively washed with 1 M sodium hydroxide, water and brine. The organic layer was dried on magnesium sulfate, filtered and then concentrated to give the product (1.33 g, 6.74 mmol, 100%) as a white needle that was used without further purification: $R_f$=0.37 (AcOEt-EP 1:19); mp: 49-50° C.; $\lambda_{max}$ (EtOH)/nm 279; IR (cm$^{-1}$) 3054, 2839, 1900, 1633, 1496, 1451, 1423, 1330, 1309, 1267, 1188, 1089, 931, 893, 782, 737; $^1$H NMR, (300 MHz, CDCl$_3$) δ 4.03 (3H, s, OCH$_3$), 6.94 (1H, d, $J_{H2\text{-}H3}$=8 Hz, H-3), 7.26 (1H, t, J=8 Hz), 7.36 (1H, t, J=7 Hz), 7.48 (1H, t, J=7 Hz), 7.54 (1H, d, J=7 Hz), 7.69 (1H, d, J=8 Hz), 7.94 (1H, d, J=8 Hz); $^{13}$C NMR, (75 MHz, CDCl$_3$) δ 56.11 (OCH$_3$), 109.31, 111.96, 112.82, 120.85, 122.86, 123.46, 124.43 (Cq), 125.72 (Cq), 127.21, 145.20 (Cq), 145.63 (Cq), 156.04 (Cq); MS (EI) m/z 199.1 M$^+$; HRMS calcd for $C_{13}H_{10}O_2$ [M+H]$^+$ 199.0754, found 199.0754.

(c) 4-Methoxy-1-nitro-dibenzofuran (9)

To a solution of 4-methoxy-dibenzofuran (3.15 g; 15.89 mmol) in glacial acetic acid (50 mL), fuming nitric acid (2.6 mL; 63.50 mmol) was added dropwise. The reaction was kept at 20° C. during the addition and stirred for 3 h. Upon completion, the reaction mixture was poured carefully onto iced water; pH was adjusted to 7 by addition of 1 M sodium hydroxide, and the product was extracted in DCM. The organic layer was dried on magnesium sulfate, filtered and then concentrated. The residue was purified by flash chromatography using ethyl acetate/EP (1:19) as eluant. The first compound to come off the column was the 4-methoxy-3-nitro-dibenzofuran (270 mg, 1.11 mmol, 7%) then the title compound (1.85 g, 7.62 mmol, 48%) was obtained as a cream solid: $R_f$=0.13 (EtOAc-EP 1:19); mp: 155-156° C.; $\lambda_{max}$ (EtOH)/nm 239; IR (cm$^{-1}$) 3092, 2917, 2851, 2042, 1876, 1630, 1568, 1506, 1438, 1396, 1342, 1297, 1274, 1239, 1205, 1159, 1129, 1091, 1002, 938, 888, 831, 812, 738, 676; $^1$H NMR, (300 MHz, CDCl$_3$) δ 4.06 (3H, s, OCH$_3$), 6.92 (1H, d, J=8 Hz), 7.18 (1H, t, J=8 Hz), 7.36 (2H, m), 8.17 (1H, d, J=8 Hz), 8.63 (1H, d, J=8 Hz); $^{13}$C NMR, (75 MHz, CDCl$_3$) δ 56.81 (OCH$_3$), 107.53, 111.81, 120.50 (Cq), 121.14 (Cq), 122.27, 123.71, 126.32, 129.55, 136.29 (Cq), 145.20 (Cq), 150.53 (Cq), 157.02 (Cq); MS (EI) m/z 243.1 M$^+$; HRMS calcd for $C_{13}H_9NO_4$ [M+H]$^+$ 243.0526, found 243.0528.

(d) 1-Nitro-dibenzofuran-4-ol (10)

4-methoxy-1-nitro-dibenzofuran (2 g, 8.22 mmol) was heated at 150° C. during 18 h in pyridine hydrochloride (17 g). The reaction was allowed to cool to 90° C., and 20 mL of water was added. Upon cooling, the product was extracted in DCM. The organic layer was dried over magnesium sulfate, filtered and then concentrated. The residue was purified by flash chromatography using DCM as eluant. The product (1.88 g, 8.22 mmol, 100%) was obtained as a yellow solid: $R_f$=0.13 (AcOEt-EP 1:4); mp: 175° C.; $\lambda_{max}$ (EtOH)/nm 239; IR (cm$^{-1}$) 1626, 1577, 1487, 1442, 1273, 1240, 1197, 1153, 1076, 1016, 983, 912, 817; $^1$H NMR, (300 MHz, CDCl$_3$) δ 6.35 (1H, s, OH), 7.03 (1H, d, J=8 Hz), 7.42 (1H, m, J=8 Hz), 7.56 (2H, m), 8.18 (1H, d, J=8 Hz), 8.70 (1H, d, J=8 Hz); $^{13}$C NMR, (75 MHz, CDCl$_3$) δ 111.69, 112.56, 120.85 (Cq), 121.56 (Cq), 122.57, 124.00, 126.72, 129.83, 136.30 (Cq), 143.98 (Cq), 146.79 (Cq), 156.99 (Cq); MS (EI) m/z 229.1 M$^+$; HRMS calcd for $C_{12}H_7NO_4$ [M+H]$^+$ 229.0370, found 229.0369.

(e) Trifluoro-methanesulfonic acid 1-nitro-dibenzofuran-4-yl ester (11)

1-Nitro-dibenzofuran-4-ol (3.01 g; 13.36 mmol was solubilised in DCM (50 mL), cooled to −40° C. and triethylamine (5.5 mL, 40 mmol) was added. After 5 min, triflic anhydride (3.45 mL, 20 mmol) was added dropwise to the reaction mixture. The temperature of the reaction mixture was kept under −30° C. during the addition. After 3 h, the reaction mixture was washed with a saturated solution of sodium carbonate (50 mL) and extracted with DCM (3×30 mL). The organic layer was dried over magnesium sulfate and evaporated to yield a brown solid. This solid was purified on a silica plug using DCM/EP (6:4) as eluant to furnish the title compound (4.536 g, 12.56 mmol, 94%) as a white solid: $R_f$=0.33

(DCM-EP 1:4); mp: 102-103° C.; λ$_{max}$ (EtOH)/nm 243; IR (cm$^{-1}$) 1643, 1572, 1528, 1488, 1427, 1348, 1317, 1246, 1209, 1132, 1068, 981, 921, 828, 792, 742, 700; $^1$H NMR, (300 MHz, CDCl$_3$) δ 7.39 (1H, m); 7.55 (1H, d, J=8 Hz); 7.65 (2H, m); 8.20 (1H, d, J=8 Hz); 8.51 (1H, d, J=8 Hz); $^{13}$C NMR, (75 MHz, CDCl$_3$) δ 112.35, 117.12 (CF$_3$), 119.49, 120.55 (CF$_3$), 120.75, 121.38 (CF$_3$), 122.81 (CF$_3$), 124.92, 126.60, 131.24, 137.88 (Cq), 142.32 (Cq), 148.21 (Cq), 157.99 (Cq); MS (EI) m/z 361.1 M$^+$; HRMS calcd for C$_{13}$H$_6$F$_3$NO$_6$S [M+H]$^+$ 360.9862, found 360.9861.

(f) 1-Nitro-4-(4,4,5,5-tetramethyl-1,3,2-dioxaborolan-2-yl)dibenzofuran (12)

In a Schlenk tube, bis(pinacolato)diboron (3.075 mg, 12.11 mmol) and potassium acetate (1.17 g, 18.16 mmol) were solubilised in dioxane (10 mL) and degassed. Concurrently, 4-hydroxy-1-nitro-dibenzofuran 4-O-triflate (2.186 g, 6.05 mmol), PdCl$_2$dppf (247 mg, 0.30 mmol) and dppf (167 mg, 0.30 mmol) were solubilised in dioxane (10 mL) and degassed. The solutions were mixed together in the Schlenk tube, stirred and heated at 110° C. for 18 h. Upon cooling, DCM (20 mL) was added. The solution was washed with water (20 mL), then dried on magnesium sulfate and evaporated. The residue was purified by flash chromatography using DCM/EP (6:4) as eluant and realising a gradient toward DCM/AcOH (98:2) to recover the entire product striking to the column. The product was concentrated, and washed with sodium carbonate (3×20 mL) to remove the acetic acid. After evaporation, the product (1.783 mg, 5.26 mmol, 87%) was recrystallised in DCM and obtained as yellow crystals: R$_f$=0.30 (AcOEt-EP 1:49); mp: 185° C.; λ$_{max}$ (EtOH)/nm 347; IR (cm$^{-1}$) 2981, 1701, 1624, 1597, 1521, 1474, 1447, 1369, 1329, 1309, 1192, 1172, 1137, 1043, 979, 883, 852, 818, 785, 754, 732, 663; $^1$H NMR, (300 MHz, CDCl$_3$) δ 1.48 (12H, s, 4×CH$_3$), 7.46 (1H, t, J=6 Hz), 7.63 (1H, t, J=6 Hz), 7.76 (1H, d, J=9 Hz), 8.01 (1H, d, J=9 Hz), 8.19 (1H, t, J=9 Hz), 8.66 (1H, d, J=9 Hz); $^{13}$C NMR, (125 MHz, CDCl$_3$) δ 24.82 (4×CH$_3$), 84.78 (2×Cq-O), 112.14, 118.07 (Cq), 118.61, 120.29 (Cq), 123.42, 125.82, 129.47, 133.50, 144.81 (Cq), 157.33 (Cq), 161.39 (Cq); MS (EI) m/z 339.2 M$^+$; HRMS calcd for C$_{18}$H$_{18}$BNO$_5$ [M+H]$^+$ 339.1273, found 339.1270.

(iii) Synthesis of 9-triflate-2-morpholin-4-yl-pyrido [2,1-a]pyrimidin-4-one (17)

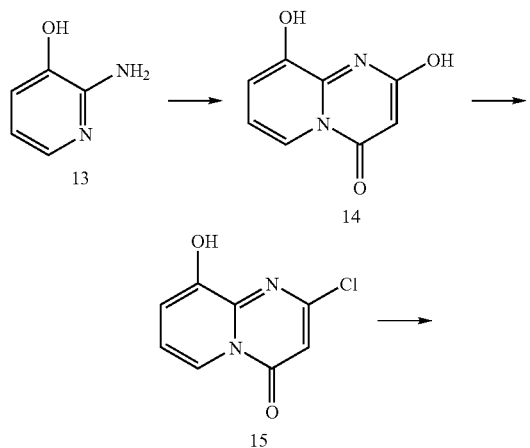

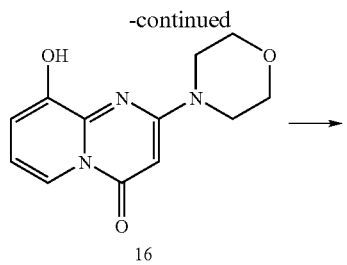

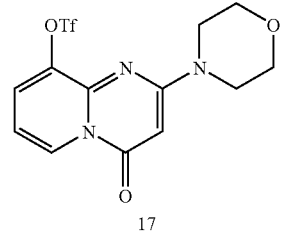

(a) 2,9-dihydroxy-pyrido[2,1-a]pyrimidin-4-one (14)

A mixture of malonic acid bis-(2,4,6-trichloro-phenyl) ester (17.33 g; 37.5 mmol) and 3-hydroxy-2-amino-pyridine (13)(4.12 g; 37.5 mmol) dissolved in bromobenzene (37 mL) was heated at reflux for 3 hours. Upon cooling, the reaction mixture was filtered and the solid was washed with ethanol. The solid was solubilised in 1M NaOH and drops of AcOH were added to precipitate the product as a pale yellow solid (6.53 g). Yield=98%. m.p.: 320° C. (degradation); R$_f$=0.11, MeOH:DCM (3:17); UV: λ$_{max}$=252 nm; IR: (cm$^{-1}$) 2862, 1688, 1564, 1374, 1295, 1102, 783; $^1$H NMR, (DMSO, 300 MHz), δ (ppm): 5.22 (1H, s, CH-3), 7.12 (1H, t, J$_{H6-H7}$=7 Hz, H$_{arom}$-7), 7.27 (1H, d, J$_{H7-H8}$=8 Hz, H$_{arom}$-8), 8.43 (1H, d, J$_{H6-H7}$=7 Hz, H$_{arom}$-6); $^{13}$C NMR, (CDCl$_3$, 75 MHz), δ (ppm): 103.25, 116.46, 117.05, 119.03, 143.97, 148.82, 157.26, 157.50.

(b) 2-Chloro-9-hydroxy-pyrido[2,1-a]pyrimidin-4-one (15)

In a round bottom flask, 2,9-dihydroxy-pyrido[2,1-a]pyrimidin-4-one (14)(1.07 g; 6.0 mmol) was dissolved in phosphorous oxychloride (7.5 mL). This solution was heated to reflux for 48 hours. Upon cooling, the reaction mixture was poured carefully into ice cold water (100 mL) and adjusted to pH 7 by addition of a saturated solution of sodium carbonate. The aqueous layer was extracted with dichloromethane. The organic layer was dried over magnesium sulphate and evaporated to yield a brown solid. This solid was purified by flash chromatography using dichloromethane as eluant to furnish the title compound as a white solid (712 mg). Yield=60%. m.p.: 162° C.; R$_f$=0.34, MeOH:DCM (1:19); Mass Spec.: (m/z) 196.93 [M+1]$^+$ (Rt=4.67 min, 12 min gradient); UV: λ$_{max}$=210 nm; IR: (cm$^{-1}$) 3103, 1684, 1630, 1511, 1458, 1297, 1105; $^1$H NMR, (CDCl$_3$, 300 MHz), δ (ppm): 6.4 (1H, s, CH-3), 7.11 (1H, t, J$_{H6-H7}$=7 Hz, H$_{arom}$-7), 7.25 (1H, d, J$_{H7-H8}$=8 Hz, H$_{arom}$-8), 8.51 (1H, d, J$_{H6-H7}$=7 Hz, H$_{arom}$-6); $^{13}$C NMR, (CDCl$_3$, 75 MHz), δ (ppm): 103.25, 116.46, 117.05, 119.03, 143.97, 148.82, 157.26, 157.50.

(c) 9-Hydroxy-2-morpholin-4-yl-pyrido[2,1-a]pyrimidin-4-one (16)

In a round bottom flask, 2-chloro-9-hydroxy-pyrido[2,1-a] pyrimidin-4-one (15)(141.7 mg; 0.721 mmol) and morpholine (314 µL; 3.605 mmol) were dissolved in ethanol (5 mL).

This solution was heated to reflux for 18 hours with vigorous stirring. Upon cooling, the solvent was evaporated. The yellow raw solid was recrystallised in ethanol, giving 173.8 mg of white crystals. Yield=97%. m.p.: 245° C.; $R_f$=0.27, MeOH: DCM (1:19); Mass Spec.: (m/z) 248.08 [M+1]$^+$ (Rt=4.92 min, 12 min gradient); UV: $\lambda_{max}$=267 nm; IR: (cm$^{-1}$) 3302, 1690, 1644, 1551, 1427, 1224, 1110; $^1$H NMR, (CDCl$_3$, 500 MHz), δ (ppm): 3.56 (4H, m, N—CH$_2$-morpholine), 3.75 (4H, m, O—CH$_2$-morpholine), 5.55 (1H, s, CH-3), 6.80 (1H, t, $J_{H6-H7}$=7 Hz, $H_{arom}$-7), 7.02 (1H, dd, $J_{H7-H8}$=8 Hz, $J_{H6-H8}$=1.3 Hz, $H_{arom}$-8), 7.33 (1H, s, OH), 8.37 (1H, dd, $J_{H6-H7}$=7 Hz, $J_{H6-H8}$=1.3 Hz, $H_{arom}$-6); $^{13}$C NMR, (CDCl$_3$, 125 MHz), δ (ppm): 45.27, 67.02, 82.16, 113.46, 114.18, 119.05, 143.00, 147.51, 159.00, 161.00.

(d) 9-Triflate-2-morpholin-4-yl-pyrido[2,1-a]pyrimidin-4-one (17)

In a three-neck round bottom flask with a thermometer, 9-hydroxy-2-morpholin-4-yl-pyrido[2,1-a]pyrimidin-4-one (16)(2.11 g; 8.54 mmol) was solubilised in DCM (70 mL), cooled to −30° C. and triethylamine (3.572 mL; 25.63 mmol) added. After 5 minutes triflic anhydride (2.101 mL; 12.81 mmol), solubilised in 10 ml of DCM, was added dropwise to the reaction mixture over 30 minutes, via an addition funnel. The temperature of the reaction mixture was kept under −20° C. during the addition. After 3 hours, the reaction mixture was washed with a saturated solution of Na$_2$CO$_3$ (50 mL) and extracted with DCM (3×30 mL). The organic layer was dried over magnesium sulphate and evaporated to yield a brown solid. This solid was purified by flash chromatography using dichloromethane as eluant to furnish the title compound as an orange solid (2.91 g). Yield=90%. m.p.: 146-147° C.; $R_f$=0.42; MeOH:DCM (1:19); Mass Spec.: (m/z) 380.16 [M+1]$^+$ (Rt=3.34 min, 12 min gradient); UV: $\lambda_{max}$=271 nm; IR: (cm$^{-1}$) 1705, 1644, 1551, 1189, 1112, 939, 769; $^1$H NMR, (CDCl$_3$, 300 MHz), δ (ppm): 3.56 (4H, m, N—CH$_2$-morpholine), 3.71 (4H, m, O—CH$_2$-morpholine), 5.53 (1H, s, CH-3), 6.80 (1H, t, $J_{H6-H7}$=7 Hz, $H_{arom}$-7), 7.46 (1H, dd, $J_{H7-H8}$=8 Hz, $J_{H6-H8}$=1.3 Hz, $H_{arom}$-8), 8.79 (1H, dd, $J_{H6-H7}$=7 Hz, $J_{H6-H8}$=1.3 Hz, $H_{arom}$-6); $^{13}$C NMR, (CDCl$_3$, 75 MHz), δ (ppm): 45.19, 66.87, 81.76, 110.16, 112.61, 116.85, 121.10, 125.34, 127.86, 128.13, 141.46, 145.79, 158.07, 160.42.

(iv) Synthesis of 8-bromo-2-morpholin-4-yl-1H-quinolin-4-one (21)

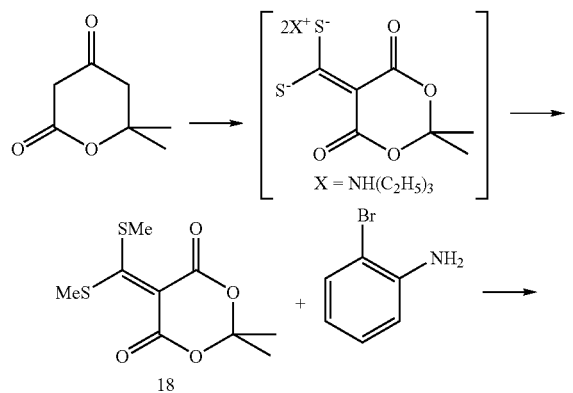

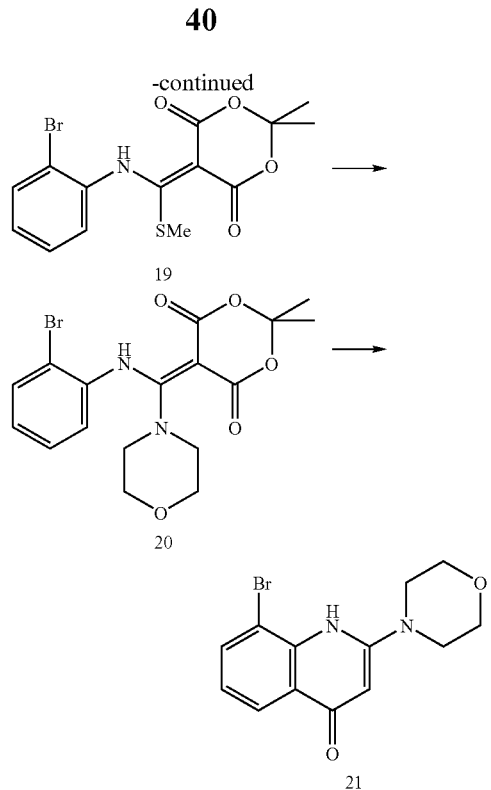

(a) 5-(Bis-methylsulfanyl-methylene)-2,2-dimethyl-[1,3]dioxane-4,6-dione (18)

In a 250 mL two neck flask, a well stirred solution of 2,2-dimethyl-1,3-dioxane-4,6-dione (12)(Meldrum's acid) (4.09 g; 28.4 mmol) in DMSO (14 mL) was formed. Triethylamine (7.92 mL; 56.8 mmol) and carbon disulfide (1.71 mL; 28.4 mmol) were added to this mixture in quick succession. The mixture was then stirred vigorously for 1 hour at room temperature before being cooled in an ice-bath. Iodomethane (3.54 mL; 56.8 mL) was slowly added to the reaction mixture with cooling (ice-bath). When the addition was completed the reaction mixture was allowed to warm to room temperature and was stirred for a further 4 hours before being diluted with ice cold water (25 mL). Scratching of the mixture precipitated the product which was filtered off and washed with petrol. The product was obtained as a yellow solid (2.76 g) and was pure enough for use in subsequent reactions. Yield=45%. m.p.: 118° C. (literature[28]: 116-118° C.); IR: (cm$^{-1}$) 3728, 1668, 1373, 1302, 1264, 1199; $^1$H NMR, (CDCl$_3$, 300 MHz), δ (ppm): 1.54 (6H, s, 2CH$_3$), 2.58 (6H, s, 2CH$_3$—S); $^{13}$C NMR, (CDCl$_3$, 75 MHz), δ (ppm): 21.86, 27.22, 103.32, 160.33, 194.

(b) 5-[2-Bromoanilino-(methylthio)-methylene]-2,2-dimethyl-4,6-dione (19)

In a 10 mL round bottom flask with cooler and nitrogen bubbler, isopropylidene bismethylthiolidene malonate (18) (900 mg; 3.63 mmol) and 2-bromoaniline (15)(624 mg; 3.63 mmol) were dissolved in 2,2,2-trifluoroethanol (3.6 mL). The mixture was stirred and heated to reflux for 22 hours. Upon cooling, the solvent was evaporated. The residue was recrystallised from methanol to yield the title compound as white crystals (1.192 g). Yield=88%. m.p.: 159° C.; $R_f$=0.31, DCM; IR: (cm$^{-1}$) 2990, 1706, 1653, 1535, 1370, 1199; UV:

λ$_{max}$=313 nm; $^1$H NMR, (CDCl$_3$, 300 MHz), δ (ppm): 1.69 (6H, s, 2CH$_3$), 2.15 (3H, s, CH$_3$—S), 7.18 (1H, dt, J$_{H4-H5}$=8 Hz, J$_{H4-H6}$=2 Hz, H$_{arom}$-4), 7.35 (2H, m, H$_{arom}$-5 and H$_{arom}$-6) 7.61 (1H, dd, J$_{H3-H4}$=8 Hz, J$_{H3-H5}$=1.2 Hz, H$_{arom}$-3), 12.51 (1H, s, N—H); $^{13}$C NMR, (CDCl$_3$, 75 MHz), δ (ppm): 18.75, 26.48, 87.54, 103.32, 120.45, 127.78, 128.46, 129.48, 133.57, 136.91, 163.87, 178.70.

(c) 5-[(2-Bromo-anilino)-morpholin-4-yl-methylene]-2,2-dimethyl-[1,3]dioxane-4,6-dione (20)

In a 10 mL round bottom flask with cooler and nitrogen bubbler, 5-[2-bromoanilino-(methylthio)-methylene]-2,2-dimethyl-4,6-dione (19)(234 mg; 0.629 mmol) and morpholine (110 μL; 1.257 mmol) were dissolved in 2,2,2-trifluoroethanol (1 mL). The mixture was stirred and heated to reflux for 18 hours. Upon cooling, the solvents were evaporated. The residue was recrystallised from methanol to yield the title compound as white crystals (0.124 g). Yield=50%. m.p.: 212-213° C.; R$_f$=0.05; DCM; IR: (cm$^{-1}$) 1627, 1342, 1305, 1100, 1022, 934; UV: λ$_{max}$=241 nm; $^1$H NMR, (CDCl$_3$, 300 MHz), δ (ppm): 1.77 (6H, s, 2CH$_3$), 3.24 (4H, t, J$_{ab}$=5 Hz, 2CH$_2$—N morpholine), 3.66 (4H, t, J$_{ab}$=5 Hz, 2CH$_2$—O morpholine), 7.18 (2H, m, H$_{arom}$-4 and H$_{arom}$-6), 7.40 (1H, t, J$_{H5-H6}$=8 Hz, H$_{arom}$-5), 7.69 (1H, dd, J$_{H3-H4}$=8 Hz, J$_{H3-H5}$=1.4 Hz, H$_{arom}$-3), 9.62 (1H, s, N—H); $^{13}$C NMR, (CDCl$_3$, 75 MHz), δ (ppm): 26.83, 51.14, 65.62, 87.54, 102.84, 120.45, 127.15, 128.92, 129.03, 134.48, 138.46, 164.92, 178.70.

(d) 8-Bromo-2-morpholin-4-yl-1H-quinolin-4-one (21)

In a Schlenk tube, 5-[(2-bromo-anilino)-morpholin-4-yl-methylene]-2,2-dimethyl-[1,3]dioxane-4,6-dione (20)(103.3 mg; 0.2513 mmol) was dissolved in diphenyl ether (0.7 mL). The mixture was stirred and heated to reflux for 4 hours. Upon cooling, petroleum ether was added. The product was collected by suction. The residue was purified by flash chromatography using dichloromethane/methanol (95:5) as eluant. The product was obtained as a brown oil (65.1 mg). Yield=84%. R$_f$=0.25, MeOH:DCM (1:19); Mass Spec.: (m/z) 310.98 [M+1]$^+$ (Rt=5.24 min, 12 min gradient); IR: (cm$^{-1}$) 3395, 2959, 2849, 1617, 1577, 1487, 1421, 1384, 1327, 1263, 1229, 1188, 1152, 1111, 1066, 999, 902, 785; UV: λ$_{max}$=254 nm; $^1$H NMR, (CDCl$_3$, 300 MHz), δ (ppm): 3.72 (4H, t, J$_{ab}$=5 Hz, 2CH$_2$—N morpholine), 3.75 (4H, t, J$_{ab}$=5 Hz, 2CH$_2$—O morpholine), 5.95 (1H, s, H-3), 7.04 (1H, t, J$_{H6-H7}$=8 Hz, H$_{arom}$-6), 7.69 (1H, dd, J$_{H6-H7}$=8 Hz, J$_{H5-H7}$=1.3 Hz, H$_{arom}$-7), 8.09 (1H, d, J$_{H5-H6}$=8 Hz, H$_{arom}$-5); $^{13}$C NMR, (CDCl$_3$, 75 MHz), δ (ppm): 46.35, 66.59, 92.50, 114.53, 123, 123.50, 124.73, 134.45, 138, 156.06, 172.6.

(v) Synthesis of 9-(1-Amino-dibenzothiophen-4-yl)-2-morpholin-4-yl-pyrido[2,1-a]pyrimidin-4-one (23)

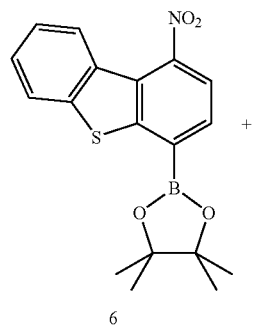

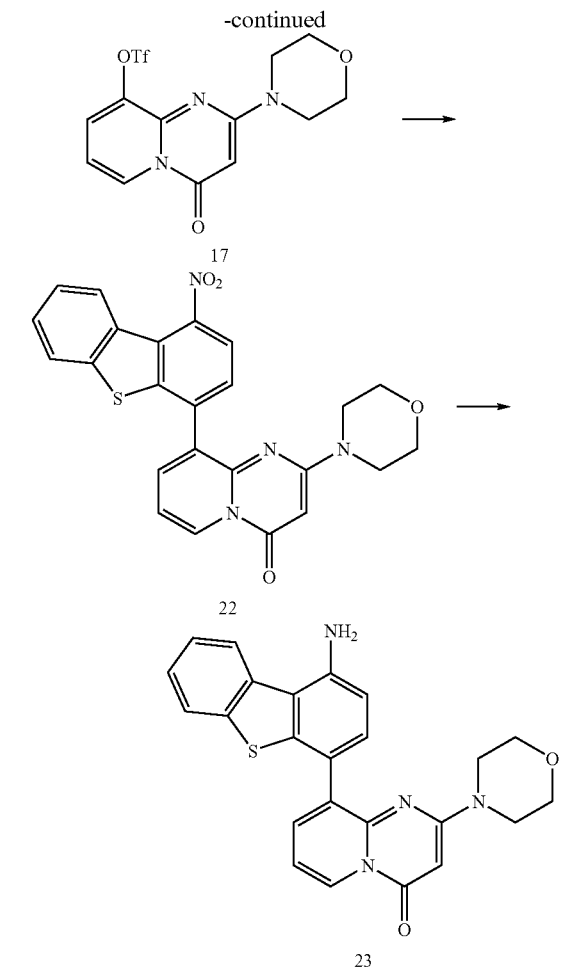

(a) 9-(1-Nitro-dibenzothiophen-4-yl)-2-morpholin-4-yl-pyrido[2,1-a]pyrimidin-4-one (22)

In a Schlenk tube, 1-nitro-4-(4,4,5,5-tetramethyl-1,3,2-dioxaborolan-2-yl)dibenzothiophene (7)(983 mg; 2.8 mmol) and caesium carbonate (2.705 g; 8.3 mmol) were solubilised in THF (8 mL). Argon was bubbled in to the solution, which was sonicated for 15 minutes. Concurrently, 9-triflate-2-morpholin-4-yl-pyrido[2,1-a]pyrimidin-4-one (6)(1.154 g; 3.045 mmol) and PdCl$_2$dppf (112.7 mg; 0.138 mmol) were solubilized in THF (8 mL). Argon was bubbled in to the solution, which was sonicated for 15 minutes. The solutions were mixed together in the Schlenk tube, stirred and heated at 80° C. for 18 hours. Upon cooling, DCM (20 mL) was added. The solution was washed with water (20 mL), then dried on magnesium sulphate and evaporated. The residue was purified by flash chromatography using ethyl acetate/DCM (1:1) as eluant. After evaporation, the product was obtained as a yellow solid (1.168 g). Yield=92%. R$_f$=0.37; AcOEt:DCM (1:1); Mass Spec.: (m/z) 459.3 [M+1]$^+$ (Rt=4.69 min)

(b) 9-(1-Amino-dibenzothiophen-4-yl)-2-morpholin-4-yl-pyrido[2,1-a]pyrimidin-4-one (23)

In a round bottom flask, 9-(1-nitro-dibenzothiophen-4-yl)-2-morpholin-4-yl-pyrido[2,1-a]pyrimidin-4-one (17) (618.8 mg; 1.351 mmol) was suspended in AcOH (10 mL). Zinc powder (883.3 mg; 13.51 mmol) was added to this solution and the reaction was stirred at room temperature overnight. The reaction mixture was filtered through Celite™, washed successively with methanol (4×50 mL) and DCM (4×50 mL). The combined organic layers were evaporated under reduced pressure. The residue was stirred with water (100 mL) and aqueous ammonia (25 mL) was added to the solution. The resultant precipitate was collected by filtration. The residue was dried and did not require further purification. The product was obtained as a yellow solid (575.3 mg). Yield=99%. $R_f$=0.36; AcOEt:DCM (1:1); Mass Spec.: (m/z) 429.47 $[M+1]^+$ (Rt=4.17 min)

(vi) Synthesis of 8-(1-amino-dibenzothiophen-4-yl)-2-morpholin-4-yl-1H-quinolin-4-one (25)

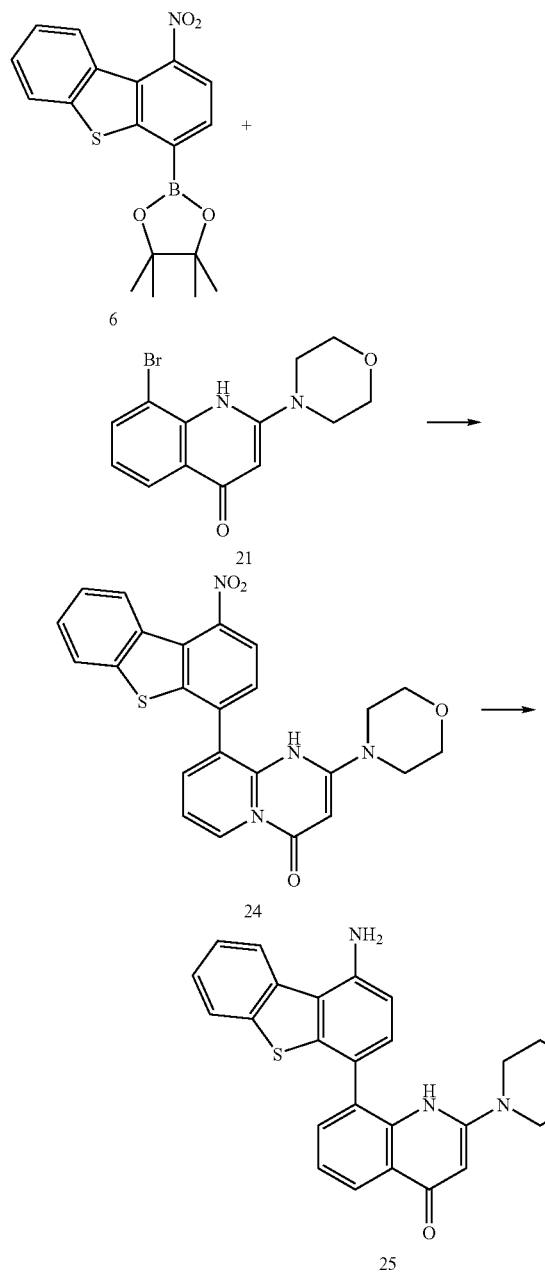

(a) 2-Morpholin-4-yl-8-(1-nitro-dibenzothiophen-4-yl)-1H-quinolin-4-one (24)

In a Schlenk tube, 1-nitro-4-(4,4,5,5-tetramethyl-1,3,2-dioxaborolan-2-yl)dibenzothiophene (6)(983 mg; 2.768 mmol) and caesium carbonate (2.705 g; 8.3047 mmol) were solubilised in THF (8 mL). Argon was bubbled in to the solution, which was sonicated for 15 minutes. Concurrently, 8-bromo-2-morpholin-4-yl-1H-quinolin-4-one (21) (941.4 mg; 3.045 mmol) and PdCl$_2$dppf (112.7 mg; 0.138 mmol) were solubilized in THF (8 mL). Argon was bubbled in to the solution, which was sonicated for 15 minutes. The solutions were mixed together in the Schlenk tube, stirred and heated at 80° C. for 18 hours. Upon cooling, DCM (20 mL) was added. The solution was washed with water (20 mL), then dried on magnesium sulphate and evaporated. The residue was purified by flash chromatography using ethyl acetate/DCM (1:1) as eluant. After evaporation, the product was obtained as a yellow solid (255.5 mg). Yield=20%. $R_f$=0.24, AcOEt:DCM (1:1); Mass Spec.: (m/z) 458.4 $[M+1]^+$ (Rt=5.33 min)

(b) 8-(1-amino-dibenzothiophen-4-yl)-2-morpholin-4-yl-1H-quinolin-4-one (25)

In a round bottom flask, 2-morpholin-4-yl-8-(1-nitro-dibenzothiophen-4-yl)-1H-quinolin-4-one (24)(365 mg; 0.798 mmol) was suspended in AcOH (5 mL). Zinc powder (5223.3 mg; 7.98 mmol) was added to this solution and the reaction was stirred at room temperature overnight. The reaction mixture was filtered through Celite™, washed successively with methanol (4×25 mL) and DCM (4×25 mL). The combined organic layers were evaporated under reduced pressure. The residue was stirred with water (50 mL) and aqueous ammonia (15 mL) was added to the solution. The resultant precipitate was collected by filtration. The residue was dried and did not require further purification. The product was obtained as a yellow solid (291.3 mg). Yield=85.4%. Mass Spec.: (m/z) 428.4 $[M+1]^+$ (Rt=3.83 min).

(vii) Synthesis of 9-(1-Amino-dibenzofuran-4-yl)-2-morpholin-4-yl-pyrido[2,1-a]pyrimidin-4-one (27)

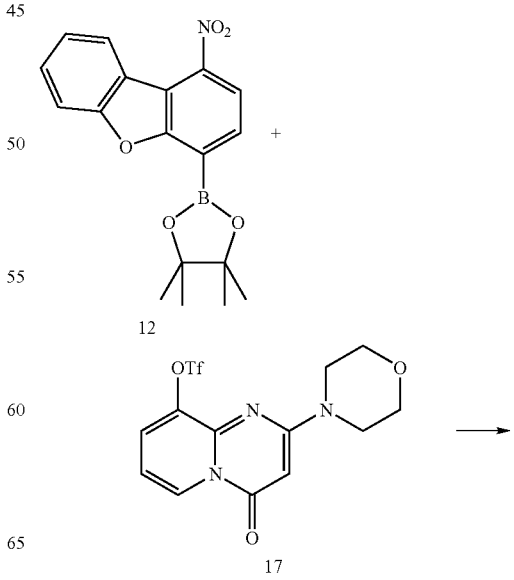

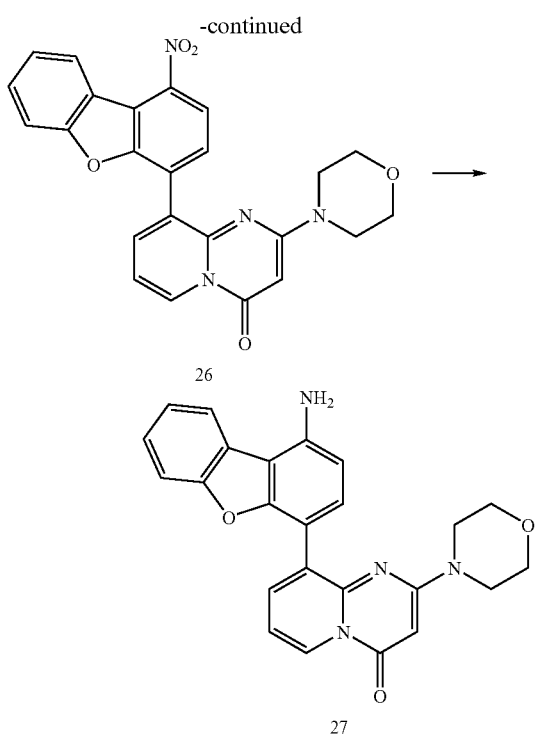

(a) 9-(1-Nitro-dibenzothiophen-4-yl)-2-morpholin-4-yl-pyrido[2,1-a]pyrimidin-4-one (26)

In a Schlenk tube, 1-nitro-4-(4,4,5,5-tetramethyl-1,3,2-dioxaborolan-2-yl)dibenzofuran (12) (500 mg, 1.47 mmol) and potassium carbonate (480 mg, 3.69 mmol) were solubilised in dioxane (10 mL) and degassed. Concurrently, 9-hydroxy-2-morpholin-4-yl-pyrido[1,2-a]pyrimidin-4-one 9-O-triflate (17) (466 mg, 1.23 mmol) and Pd(PPh$_3$)$_4$ (71 mg, 0.06 mmol) were solubilised in dioxane (10 mL) and degassed. The solutions were mixed together in a microwave vessel, which was placed into the microwave reactor at 180° C. for 30 min. Upon cooling, DCM (20 mL) was added. The solution was washed with water (20 mL), then dried on magnesium sulfate and evaporated. The residue was triturated in hot methanol, and the product (375 mg, 0.85 mmol, 69%) was filtered off as a brown solid: R$_f$=0.51 (AcOEt); mp: 262° C.; λ$_{max}$ (EtOH)/nm 268; IR (cm$^{-1}$) 1706, 1673, 1631, 1599, 1541, 1511, 1430, 1338, 1306, 1230, 1194, 1116, 1070, 1028, 999, 975, 860; $^1$H NMR, (300 MHz, CDCl$_3$) δ 3.26 (4H, m, 2×N—CH$_2$-morpholine), 3.47 (4H, m, 2×O—CH$_2$-morpholine), 5.57 (1H, s, H-3), 7.03 (1H, t, J$_{H6-H7}$=7 Hz, H-7), 7.44 (1H, t, J=7 Hz), 7.58 (2H, m), 7.74 (1H, d, J=7 Hz), 7.86 (1H, d, J=7 Hz), 8.24 (1H, d, J=8 Hz), 8.66 (1H, d, J=8 Hz), 9.10 (1H, d, J=8 Hz, H-6); $^{13}$C NMR, (125 MHz, CDCl$_3$) δ 44.41 (2×CH$_2$—N-morpholine), 66.32 (2×CH$_2$—O-morpholine), 81.09 (C-3), 111.58, 112.05, 119.26, 120.67, 123.89, 126.28, 127.57, 128.32, 128.76, 128.95, 130.01, 138.39, 142.88, 143.92, 148.48, 154.66, 157.04 (Cq), 158.67 (Cq), 160.28 (Cq); MS (EI) m/z 443.35 M$^+$; HRMS calcd for C$_{24}$H$_{19}$N$_4$O$_5$ [M+H]$^+$ 443.1350, found 443.1352.

(b) 9-(1-Amino-dibenzofuran-4-yl)-2-morpholin-4-yl-pyrido[2,1-a]pyrimidin-4-one (27)

In a round bottom flask, 9-(1-nitro-dibenzofuran-4-yl)-2-morpholin-4-yl-pyrido[1,2-a]pyrimidin-4-one (26) (300 mg, 0.68 mmol) was suspended in AcOH (5 mL). Zinc powder (445 mg, 6.8 mmol) was added to this solution and the reaction was stirred at room temperature overnight. The reaction mixture was filtered through celite and washed successively with methanol (4×50 mL) and DCM (4×50 mL). The combined organic layers were evaporated under reduced pressure. The residue was stirred with water (100 mL), and aqueous ammonia (25 mL) was added to the solution. The resultant precipitate was collected by filtration. This solid was purified by flash chromatography using AcOEt as eluant to furnish the title compound (269 mg, 0.65 mmol, 96%) as a white solid: R$_f$=0.32 (AcOEt); mp: 294° C.; λ$_{max}$ (EtOH)/nm 238; IR (cm$^{-1}$) 3340, 3224, 2937, 2872, 2258, 1697, 1637, 1623, 1543, 1493, 1440, 1373, 1309, 1258, 1234, 1191, 1150, 1109, 1073, 999, 909, 856, 776; $^1$H NMR, (300 MHz, MeOD) δ 3.36 (4H, m, 2×N—CH$_2$-morpholine), 3.52 (4H, m, 2×O—CH$_2$-morpholine), 6.72 (1H, d, J=7 Hz), 6.88 (1H, t, J=7 Hz), 7.31-7.47 (5H, m), 7.90 (2H, m), 8.90 (1H, d, J=7 Hz); $^{13}$C NMR, (75 MHz, MeOD) δ 46.23 (2×CH$_2$—N-morpholine), 68.02 (2×CH$_2$—O-morpholine), 110.44, 112.78, 114.57, 122.46, 124.53, 125.58 (Cq), 127.53, 128.01, 131.81, 133.58, 138.88, 145.06 (Cq), 150.82 (Cq), 156.70 (Cq), 156.90 (Cq), 161.68 (Cq), 162.11 (Cq); MS (EI) m/z 413.19 M$^+$; Anal. Calcd for 0.86 mol C$_{24}$H$_{20}$N$_4$O$_3$+0.14 mol MeOH: C, 69.48, H, 4.99, N, 13.41. Found: C, 69.22, H, 4.79, N, 13.38; HRMS calcd for C$_{24}$H$_{21}$N$_4$O$_3$ [M+H]$^+$ 413.1608, found 413.1609.

(viii) Synthesis of 9-(1-Amino-dibenzofuran-4-yl)-2-morpholin-4-yl-pyrido[2,1-a]pyrimidin-4-one (29)

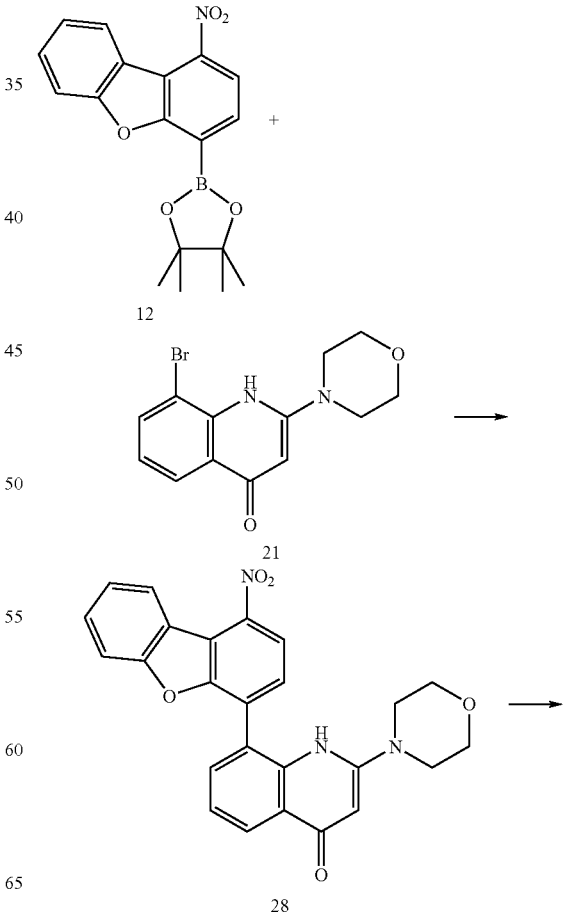

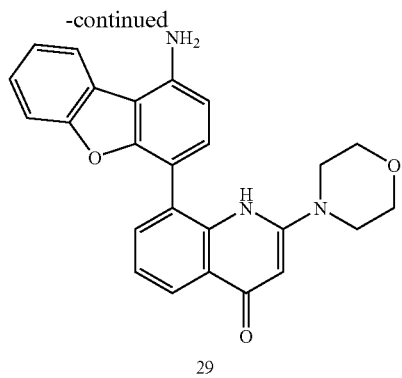

(a) 2-Morpholin-4-yl-8-(1-nitro-dibenzofuran-4-yl)-1H-quinolin-4-one (28)

In a Schlenk tube, 1-nitro-4-(4,4,5,5-tetramethyl-1,3,2-dioxaborolan-2-yl)dibenzofuran (12) (500 mg, 1.47 mmol) and potassium carbonate (480 mg, 3.69 mmol) were solubilised in dioxane (10 mL) and degassed. Concurrently, 8-bromo-2-morpholin-4-yl-1H-quinolin-4-one (21) (380 mg, 1.23 mmol) and Pd(PPh$_3$)$_4$ (71 mg, 0.06 mmol) were solubilised in dioxane (10 mL) and degassed. The solutions were mixed together in a microwave vessel, which was placed into the microwave reactor at 180° C. for 30 min. Upon cooling, DCM (20 mL) was added. The solution was washed with water (20 mL), then dried on magnesium sulfate and evaporated. The residue was purified by flash chromatography using AcOEt/EP (8:2) as eluant to furnish the title compound (303 mg, 0.74 mmol, 60%) as a yellow solid: R$_f$=0.67 (AcOEt); mp: 247° C.; λ$_{max}$(EtOH)/nm 251; IR (cm$^{-1}$) 3421, 2852, 2360, 2333, 1614, 1573, 1500, 1435, 1429, 1348, 1309, 1233, 1199, 1152, 1124, 1039, 991, 917, 866, 823; $^1$H NMR, (300 MHz, CDCl$_3$) δ 3.04 (4H, m, 2×CH$_2$—N-morpholine), 3.54 (4H, m, 2×CH$_2$—O-morpholine), 5.92 (1H, s, H-3), 7.19-7.45 (2H, m), 7.51-7.58 (2H, m), 7.65-7.70 (2H, m), 8.31 (2H, m), 8.67 (1H, d, J=7 Hz); MS (EI) m/z 442.29 M$^+$; HRMS calcd for C$_{25}$H$_{20}$N$_3$O$_5$ [M+H]$^+$ 442.1397, found 442.1398.

(b) 8-(1-amino-dibenzofuran-4-yl)-2-morpholin-4-yl-1H-quinolin-4-one (29)

In a round bottom flask, 2-morpholin-4-yl-8-(1-nitro-dibenzothiophen-4-yl)-1H-quinolin-4-one (28) (290 mg, 0.66 mmol) was suspended in acetic acid (5 mL). Zinc powder (430 mg, 6.58 mmol) was added to this solution and the reaction was stirred at room temperature overnight. The reaction mixture was filtered through celite and then washed successively with methanol (4×25 mL) and DCM (4×25 mL). The combined organic layers were evaporated under reduced pressure. The residue was stirred with water (50 mL), and aqueous ammonia (15 mL) was added to the solution. The resultant precipitate was collected by filtration. The residue was dried and did not require further purification. The product (246 mg, 0.60 mmol, 91%) was obtained as a brown oil: R$_f$=0.44 (AcOEt); λ$_{max}$ (EtOH)/nm 315; IR (cm$^{-1}$) 1708, 1572, 1374, 1278, 1190, 1116, 1049, 1010, 931, 880, 827, 748, 722, 688, 688; $^1$H NMR, (300 MHz, CDCl$_3$) δ 3.11 (4H, m, 2×CH$_2$—N-morpholine), 3.58 (4H, m, 2×CH$_2$—O-morpholine), 5.98 (1H, s, H-3), 6.85 (1H, d, J=8 Hz), 7.25-7.51 (3H, m), 7.52-7.68 (3H, m), 8.05 (1H, t, J=8 Hz), 8.67 (1H, d, J=8 Hz); $^{13}$C NMR, (75 MHz, MeOD) δ 48.02 (2×CH$_2$—N-morpholine), 67.44 (2×CH$_2$—O-morpholine), 111.94, 112.63, 122.96, 125.05, 125.57, 127.63, 127.87, 131.55, 132.68, 135.32, 146.21, 156.79; MS (EI) m/z 412.25 M$^+$; HRMS calcd for C$_{25}$H$_{22}$N$_3$O$_3$ [M+H]$^+$ 412.1656, found 412.1654.

(ix) Synthesis of 9-(1-Hydroxy-dibenzothiophen-4-yl)-2-morpholin-4-yl-pyrido[2,1-a]pyrimidin-4-one (31)

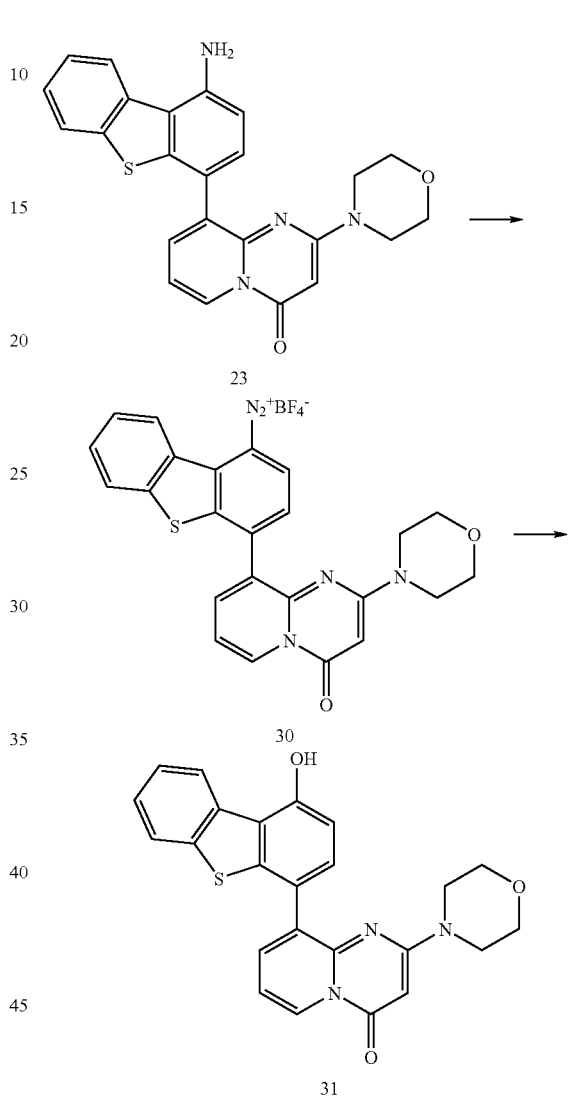

In a round bottom flask, 9-(1-amino-dibenzothiophen-4-yl)-2-morpholin-4-yl-pyrido[2,1-a]pyrimidin-4-one (23)(137.2 mg; 0.32 mmol) was suspended in ethanol (15 mL). HBF$_4$ (664 µL; 4.81 mmol) was added dropwise at room temperature. After stirring for 15 minutes, the reaction mixture became a clear solution, which was cooled at 0° C. and t-butylnitrite (76.1 µL; 0.64 mmol) was added. After 30 minutes, the reaction mixture was diluted with ether (25 mL). A precipitate was formed and was filtered off, then washed with ether (2×5 mL) and dried. This solid was added to a solution of cupric nitrate (23.193 g; 96 mmol) in water (500 mL) containing cuprous oxide (45.78 mg; 0.32 mmol) and stirred for 1 hour at room temperature. The aqueous solution was filtered to afford a brown solid. The residue was purified by flash chromatography using methanol/DCM (2:98) as eluant. The by-product due to deamination was isolated in 17% yield (22.5 mg). The product was obtained as a yellow solid (26.3 mg). Yield=19%. Mass Spec.: (m/z) 430.3 [M+1]$^+$ (Rt=4.23 min)

(x) Synthesis of 8-(1-amino-dibenzofuran-4-yl)-2-morpholin-4-yl-1-benzopyran-4-one (33)

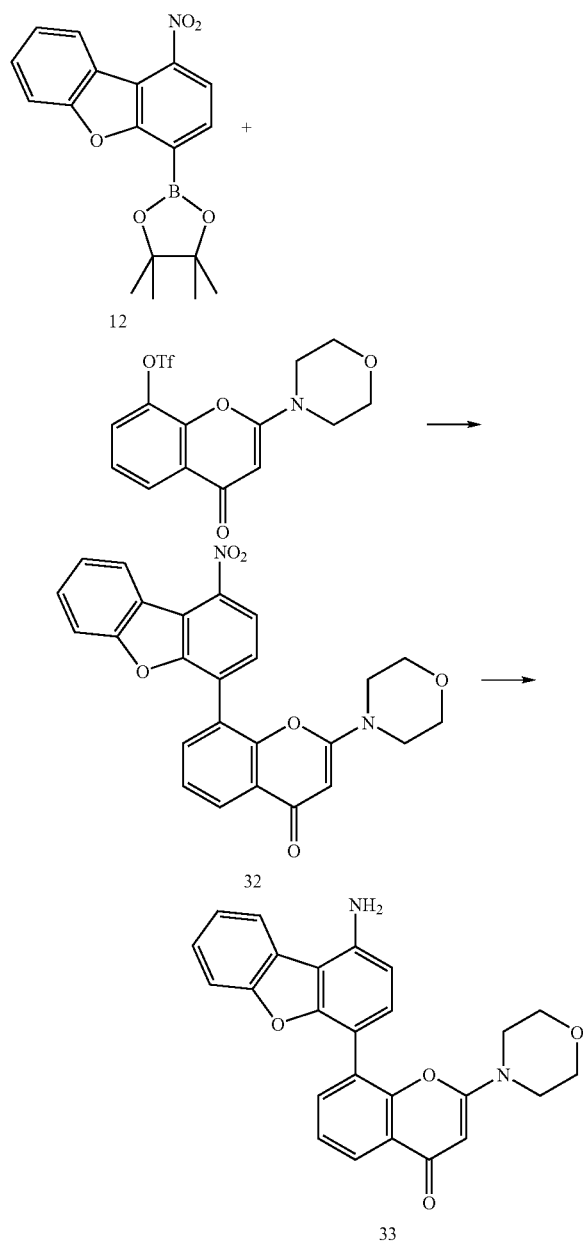

(a) 2-Morpholin-4-yl-8-(1-nitro-dibenzofuran-4-yl)-1-benzopyran-4-one (32)

To a solution of 1-nitro-4-(4,4,5,5-tetramethyl-1,3,2-dioxaborolan-2-yl)-dibenzofuran (12, 0.30 mmol, 0.10 g) in anhydrous dioxane (2 ml) was added trifluoro-methanesulfonic acid 2-morpholin-4-yl-4-oxo-4H-1-benzopyran-8-yl ester (0.24 mmol, 0.091 g, see WO 03/024949), potassium carbonate (0.6 mmol, 0.083 g) and tetrakis (triphenylphosphine) palladium (0.015 mmol, 0.018 g). The reaction vessel was sealed and heated under the influence of microwave radiation (140° C., 10 minutes, low absorption setting). Upon completion the reaction mixture was filtered through a thin pad of silica and the cake washed with $CH_2Cl_2$. The solvents were then removed in vacuo to give a light brown solid residue (0.13 g, 100%) which was used without further purification. m/z 443.4 $[M+H]^+$ (Rt=4.76 min).

(b) 8-(1-Amino-dibenzofuran-4-yl)-2-morpholin-4-yl-1-benzopyran-4-one (33)

To a solution of 2-morpholin-4-yl-8-(1-nitro-dibenzofuran-4-yl)-1-benzopyran-4-one (32, 2.5 mmol, 1.11 g) in acetic acid (50 ml) was added zinc dust (25 mmol, 1.64 g), portionwise over ten minutes. The mixture was then stirred at room temperature for 2 hrs, whereupon it was filtered through a Celite™ pad which was washed with methanol (20 ml) and $CH_2Cl_2$ (20 ml). Solvents were removed in vacuo to give a slurry which was then diluted with ammonia hydroxide (30 ml) and the resulting solid removed by filtration. The residue was purified by flash chromatography ($SiO_2$) using MeOH; $CH_2Cl_2$-1:99 as eluent to give the desired product (75%) in analytically pure form. m/z 413.5 $[M+H]^+$ (Rt=4.27 min).

Example 1

Parallel Synthesis from 9-Triflate-2-morpholin-4-yl-pyrido[2,1-a]pyrimidin-4-one (17)

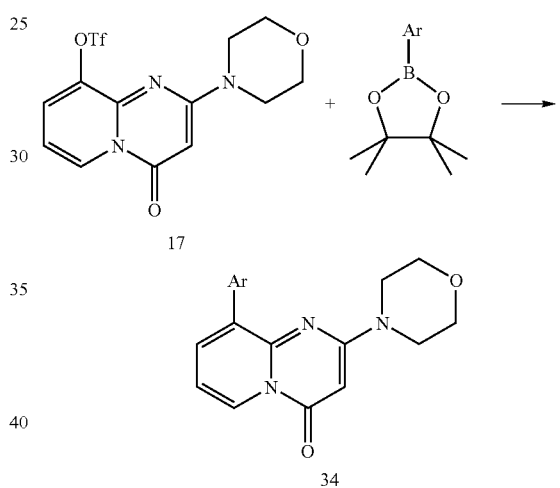

An appropriate boronic acid (0.395 mmol) and potassium carbonate (109.3 mg; 0.7914 mmol) were introduced in to a carousel tube. The flask was evacuated and purged with argon. This operation was performed 3 times. In a Schlenk tube, 9-triflate-2-morpholin-4-yl-pyrido[2,1-a]pyrimidin-4-one (17)(100 mg; 0.2638 mmol; per carousel tube) was solubilized in dioxane (2 mL; per carousel tube). Argon was bubbled in to the solution, which was sonicated for 15 minutes. In another Schlenk tube, terakis-(triphenylphosphine)-palladium (15.2 mg; 0.013 mmol; per carousel tube) was solubilized in dioxane (2 mL; per carousel tube). Argon was bubbled in to the solution, which was sonicated for 15 minutes. 2 mL of each solution was mixed together in the carousel tube, stirred and heated at 95° C. for 48 hours. Upon cooling, the solution was filtered through a Radleys Discovery Technologie solid phase extraction column of 500 mg of silica, which was placed on a stalker parallel purification system. The column was washed with ethyl acetate (20 mL), and collected as Phase 1. The column was then washed with dichloromethane/methanol (85:15) (20 mL) and collected as Phase 2. Both phases were checked for product via LC/MS. In some cases, phase 2 contained only impurities, in other cases both phases were combined and evaporated. Depending on the product, the purification was performed by HPLC or by flash chromatography.

| Compound | Ar |
|---|---|
| 34a | (dibenzothiophene) |
| 34b | (dibenzofuran) |

NMR Results

34a: $^1$H NMR, (CDCl$_3$, 300 MHz), δ (ppm): 3.36 (4H, m, N—CH$_2$-morpholine); 3.56 (4H, m, O—CH$_2$-morpholine); 5.64 (1H, s, CH-3); 7.01 (1H, t, J$_{H6-H7}$=7 Hz, H$_{arom}$-7); 7.45-7.49 (2H, m); 7.56-7.57 (2H, m); 7.79-7.82 (1H, m); 7.86-7.89 (1H, dd); 8.19-8.23 (2H, m); 9.04 (1H, dd).

$^{13}$C-NMR, (CDCl$_3$, 300 MHz), δ (ppm): 44.83 (CH$_2$—N— morpholine); 66.84 (CH—O— morpholine); 81.37 (CH-3); 112.47 (CH-7); 121.69; 122.10; 122.92; 124.62; 124.85; 127.39; 128.27; 128.91; 132.41; 134.77; 135.88; 136.36; 137.54; 139.60; 140.13; 148.84; 159.38 (Cq); 160.54 (C=O).

34b: $^1$H NMR, (CDCl$_3$, 300 MHz), δ (ppm): 3.35 (4H, t, N—CH$_2$— morpholine); 3.54 (4H, t, O—CH$_2$-morpholine); 5.66 (1H, s, CH-3); 7.08 (1H, t, J$_{H6-H7}$=7 Hz, H$_{arom}$-7); 7.38-7.51 (4H, m, H$_{arom}$-dibenzofuran); 7.67 (1H, dd, J$_{H7-H8}$=7.6 Hz, J$_{H6-H8}$=1.3 Hz, H$_{arom}$-8); 7.94 (1H, dd, J=7 Hz, J=1.6 Hz, H$_{arom}$-dibenzofuran); 8.01-8.05 (2H, m, H$_{arom}$-dibenzofuran); 9.06 (1H, dd, J$_{H6-H7}$=7 Hz, J$_{H6-H8}$=1.3 Hz, H$_{arom}$-6).

$^{13}$C-NMR, (CDCl$_3$, 300 MHz), δ (ppm): 44.80 (CH$_2$—N— morpholine); 66.80 (CH—O— morpholine); 81.37 (CH-3); 111.98; 112.65; 121.14; 121.75; 122.76; 123.31; 124.38; 124.89; 127.80; 128.03; 129.28; 131.42; 138.06; 156.30; 159.48; 160.69.

21c: $^1$H NMR, (CDCl$_3$, 300 MHz), δ (ppm): 3.42 (4H, m, N—CH$_2$-morpholine); 3.56 (4H, m, O—CH$_2$-morpholine); 5.40 (1H, s, CH-3); 6.87 (1H, t, J$_{H6-H7}$=7 Hz, H$_{arom}$-7); 7.26-7.83 (10H, m, H$_{arom}$-biphenyl and H$_{arom}$-8); 8.87 (1H, dd, J$_{H6-H7}$=7.1 Hz, J$_{H6-H8}$=1.6 Hz, H$_{arom}$-6).

Example 2

Parallel Synthesis from 8-Bromo-2-morpholin-4-yl-1H-quinolin-4-one (21)

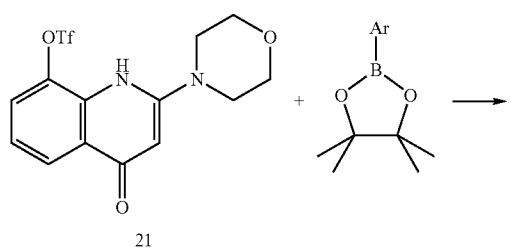

21

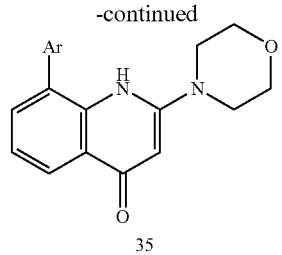

35

An appropriate boronic acid (0.486 mmol) and potassium carbonate (269.2 mg; 1.946 mmol) were introduced in to a carousel tube. The flask was evacuated and purged with argon. This operation was performed 3 times. In a Schlenk tube, 8-bromo-2-morpholin-4-yl-1H-quinolin-4-one (21)(100 mg; 0.324 mmol; per carousel tube) was solubilized in dioxane (2 mL; per carousel tube). Argon was bubbled in to the solution, which was sonicated for 15 minutes. In another Schlenk tube, terakis-(triphenylphosphine)-palladium (18.7 mg; 0.016 mmol; per carousel tube) was solubilized in dioxane (2 mL; per carousel tube). Argon was bubbled in to the solution, which was sonicated for 15 minutes. 2 mL of each solution was mixed together in the carousel tube, stirred and heated at 95° C. for 48 hours. Upon cooling, the solution was filtered through a Radleys Discovery Technologie solid phase extraction column of 500 mg of silica, which was placed on a stalker parallel purification system. The column was washed with ethyl acetate (20 mL), and collected as Phase 1. The column was then washed with dichloromethane/methanol (85:15) (20 mL), and collected as Phase 2. Both phases were checked for product via LC/MS. In some cases, phase 2 contained only impurities, in other cases both phases were combined and evaporated. Depending on the product, the purification was performed by HPLC or by flash chromatography.

| Compound | Ar |
|---|---|
| 35a | (dibenzothiophene) |
| 35b | (dibenzofuran) |

NMR Results

35a: $^1$H-NMR, (CDCl$_3$. 300 MHz), δ (ppm): 2.93 (4H, t, J=5 Hz, CH$_2$—N morpholine), 3.57 (4H, t, J=5 Hz, CH$_2$—O morpholine), 5.67 (1H, s, H-3), 7.34 (t, 1H, J=8 Hz, H$_{arom}$), 7.42-7.74 (m, 8H, H$_{arom}$), 8.15-8.23 (m, 2H, H$_{arom}$), 8.33 (d, 1H, J=8 Hz, H$_{arom}$)

$^{13}$C-NMR, (CDCl$_3$, 300 MHz), δ (ppm): 46.94 (CH$_2$—N Morpholine), 66.22 (CH$_2$—O Morpholine), 93.44 (CH-3), 122.38 (CH), 122.46 (CH), 123.30 (CH), 123.43 (CH), 124.62 (CH), 125.29 (CH), 125.80 (CH), 126.86 (CH), 127.69 (CH), 127.93 (CH), 131.22 (CH), 132.56 (CH), 135.60 (CH), 135.81 (CH), 137.41 (CH), 139.75 (CH), 140.74 (CH), 154.24 (C$_4$=O), 178.86 (C$_2$).

35b: $^1$H NMR, (CDCl$_3$, 300 MHz), δ (ppm): 2.93 (4H, s, N—CH$_2$-morpholine); 3.50 (4H, s, O—CH$_2$-morpholine); 5.69 (1H, s, CH-3); 7.19-7.45 (6H, m, H$_{arom}$-dibenzofuran and H$_{arom}$-7); 7.64 (1H, s, H$_{arom}$-8); 7.95 (3H, m, H$_{arom}$-dibenzofuran); 8.30 (1H, s, H$_{arom}$-6).

$^{13}$C-NMR, (CDCl$_3$, 300 MHz), δ (ppm): 46.87 (CH$_2$—N— morpholine); 66.27 (CH—O— morpholine); 92.17 (CH-3); 112.10; 121.44; 121.80; 123.43; 123.92; 124.42; 125.82; 126.67; 128.49; 129.11; 133.84; 136.04; 153.32; 154.44; 156.31; 178.93.

Example 3

Synthesis of 2-amino-N-[4-(2-morpholin-4-yl-4-oxo-4H-pyrido[2,1-a]pyrimidin-9-yl)-dibenzothiophen-1-yl]-acetamides (36)

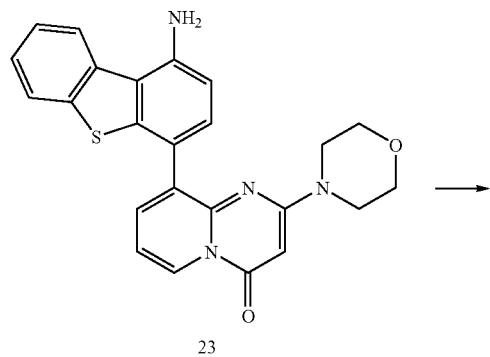

23

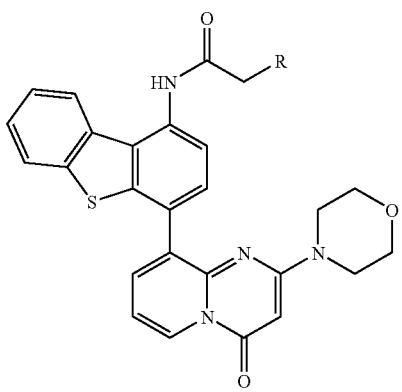

43

In a round bottom flask, 9-(1-amino-dibenzothiophen-4-yl)-2-morpholin-4-yl-pyrido[2,1-a]pyrimidin-4-one (9)(152.7 mg; 0.356 mmol) was solubilised in dry DMA (4.5 mL). Triethylamine (109.3 μL; 0.784 mmol) and chloroacetyl chloride (31.03 μL; 0.392 mmol) were added to this solution and the reaction was stirred at room temperature for 4 hours. Aliquots (0.5 mL) of the reaction product were added to each of the 9 tubes containing a different amine (3 eq) in a greenhouse workstation. The reaction mixtures were stirred in parallel at room temperature for 18 hours. Each tube was diluted with the minimum amount of methanol (max. 1.5 mL) and transferred into a LC/MS vial. All the LC/MS vials were submitted for QC and semi-preparative HPLC for purification.

| Compound | R | Purity (%) | RT (s) | Mass (M + H) |
|---|---|---|---|---|
| 36a | morpholine | 94 | 3.28 | 556.4 |
| 36b | piperazine | 80 | 3.17 | 555.4 |
| 36c | 4-(2-methoxyethyl)piperazine | 100 | 3.23 | 613.4 |
| 36d | 4-ethylpiperazine | 95 | 3.25 | 583.4 |
| 36e | 4-(pyridin-2-yl)piperazine | 70 | 3.36 | 632.2 |

-continued

| Compound | R | Purity (%) | RT (s) | Mass (M + H) |
|---|---|---|---|---|
| 36f | ![piperazine-N-methyl] | 95 | 3.18 | 569.4 |
| 36g | ![piperazine-N-ethanol] | 95 | 3.13 | 599.4 |
| 36h | ![N-methyl bis(ethanol)amine] | 90 | 3.14 | 574.3 |
| 36i | ![2,6-dimethylmorpholine] | 90 | 3.47 | 584.4 |
| 36j | ![piperazine-ethoxyethanol] | 85 | 3.18 | 643.5 |
| 36k | ![piperazine-acetamide-isopropyl] | 90 | 3.31 | 654.4 |

Example 4

Synthesis of 3-amino-N-[4-(2-morpholin-4-yl-4-oxo-4H-pyrido[2,1-a]pyrimidin-9-yl)-dibenzothiophen-1-yl]-propionamides (37)

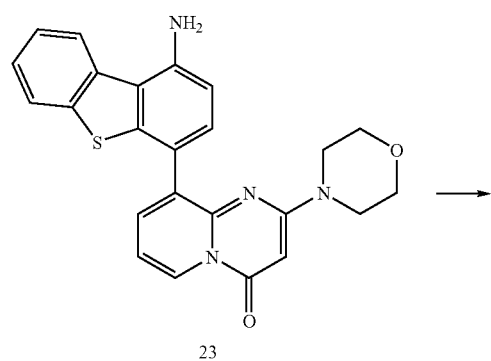

23

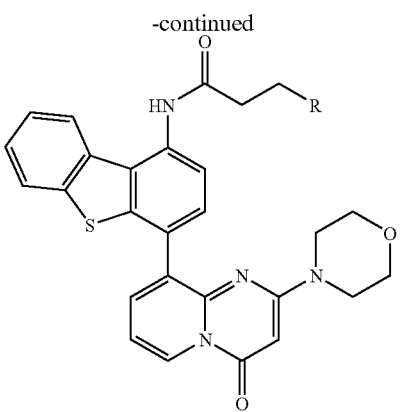

37

In a round bottom flask, 9-(1-amino-dibenzothiophen-4-yl)-2-morpholin-4-yl-pyrido[2,1-a]pyrimidin-4-one (23)(127 mg; 0.296 mmol) was solubilised in dry DMA (4 mL). Triethylamine (90.8 µL; 0.652 mmol) and 3-bromopropionyl chloride (32.8 µL; 0.326 mmol) were added to this solution and the reaction was stirred at room temperature for 4 hours. Aliquots (0.5 mL) of the reaction product were added to each of the 8 tubes containing a different amine (3 eq) in the greenhouse workstation. The reaction mixtures were stirred in parallel at room temperature for 18 hours. Each tube was diluted with the minimum amount of methanol (max. 1.5 mL) and transferred into a LC/MS vial. All the LC/MS vials were submitted for QC and semi preparative HPLC for purification.

| Compound | R | Purity (%) | RT (s) | Mass (M + H) |
|---|---|---|---|---|
| 37a | morpholine | 85 | 3.21 | 570.3 |
| 37b | 4-methoxybenzylamine | 90 | 3.53 | 620.3 |
| 37c | tetrahydrofurfurylamine | 90 | 3.31 | 584.3 |
| 37d | 3-morpholinopropylamine | 85 | 2.93 | 627.4 |
| 37e | 4-acetylpiperazine | 90 | 3.17 | 611.3 |

Example 5

Synthesis of 2-amino-N-[4-(2-morpholin-4-yl-4-oxo-1,4-dihydro-quinolin-8-yl)-dibenzothiophen-1-yl]-acetamides (38)

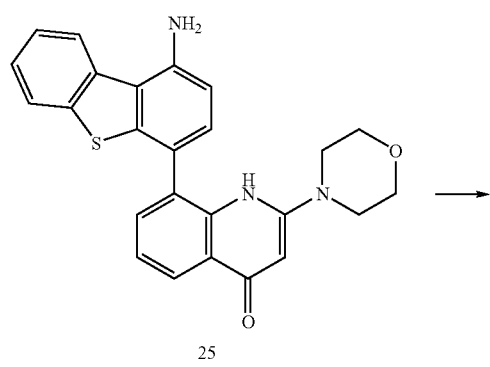

25

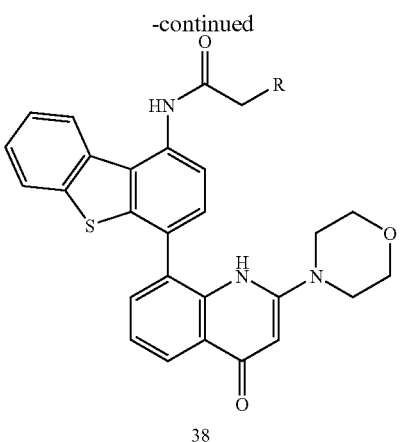

38

In a round bottom flask, 8-(1-amino-dibenzothiophen-4-yl)-2-morpholin-4-yl-1H-quinolin-4-one (25)(153.9 mg; 0.36 mmol) was solubilised in dry DMA (4.5 mL). Triethylamine (110.3 µL; 0.696 mmol) and chloroacetyl chloride (31.5 µL; 0.396 mmol) were added to this solution and the reaction was stirred at room temperature for 4 hours. Aliquots (0.5 mL) of the reaction product were added to each of the 9 tubes containing a different amine (3 eq) in a greenhouse workstation. The reaction mixtures were stirred in parallel at room temperature for 18 hours. Each tube was diluted with the minimum amount of methanol (max. 1.5 mL) and transferred into a LC/MS vial. All the LC/MS vials were submitted for QC and semi preparative HPLC for purification.

| Compound | R | Purity (%) | RT (s) | Mass (M + H) |
|---|---|---|---|---|
| 38a | NH$_2$ | 80 | 2.99 | 485.3 |
| 38b | morpholine | 95 | 3.18 | 555.4 |
| 38c | piperazine | 90 | 3.06 | 554.3 |
| 38d | 4-(2-methoxyethyl)piperazine | 90 | 3.13 | 612.4 |
| 38e | 4-ethylpiperazine | 90 | 3.1 | 582.3 |
| 38f | 4-(pyridin-2-yl)piperazine | 90 | 3.24 | 631.3 |

-continued

| Compound | R | Purity (%) | RT (s) | Mass (M + H) |
|---|---|---|---|---|
| 38g | (N-methylpiperazinyl) | 90 | 3.08 | 568.3 |
| 38h | (hydroxyethylpiperazinyl) | 90 | 3.07 | 598.3 |

Example 6

Synthesis of 3-amino-N-[4-(2-morpholin-4-yl-1H-quinolin-4-quinolin-8-yl)-dibenzothiophen-1-yl]-propionamides (39)

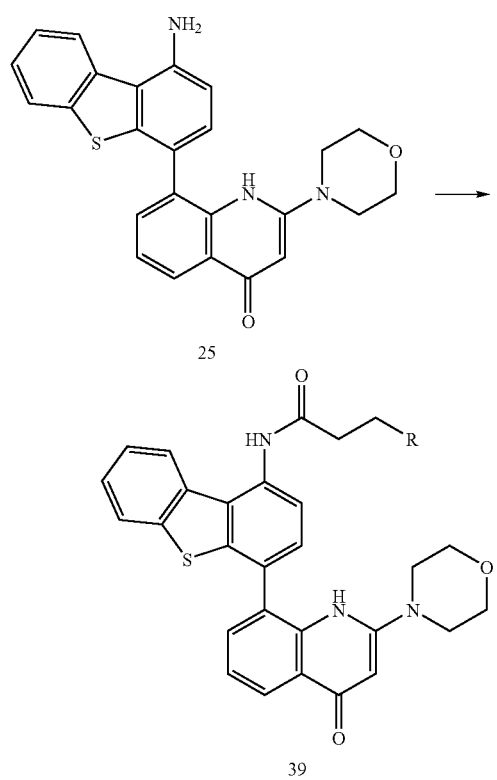

In a round bottom flask, 8-(1-amino-dibenzothiophen-4-yl)-2-morpholin-4-yl-1H-quinolin-4-one (25)(79.2 mg; 0.185 mmol) was solubilised in dry DMA (3 mL). Triethylamine (56.8 µL; 0.407 mmol) and 3-bromopropionyl chloride (20.5 µL; 0.204 mmol) were added to this solution and the reaction was stirred at room temperature for 4 hours. Aliquots (0.5 mL) of the reaction product were added to each of the 6 tubes containing a different amine (3 eq) in a greenhouse workstation. The reaction mixtures were stirred in parallel at room temperature for 18 hours. Each tube was diluted with the minimum amount of methanol (max. 1.5 mL) and transferred into a LC/MS vial. All the LC/MS vials were submitted for QC and semi preparative HPLC for purification.

| Compound | R | Purity (%) | RT (s) | Mass (M + H) |
|---|---|---|---|---|
| 39a | tetrahydrofurfurylaminomethyl | 85 | 3.22 | 583.2 |
| 39b | morpholinyl | 95 | 3.1 | 569.3 |
| 39c | azepanyl | 90 | 3.27 | 581.3 |
| 39d | piperidinyl | 95 | 3.21 | 567.3 |
| 39e | 2,6-dimethylmorpholinyl | 90 | 3.21 | 597.3 |
| 39f | 4-acetylpiperazinyl | 90 | 3.13 | 610.4 |

Example 7

Synthesis of 2-amino-N-[4-(2-morpholin-4-yl-4-oxo-4H-pyrido[2,1-a]pyrimidin-9-yl)-dibenzofuran-1-yl]-acetamides (40)

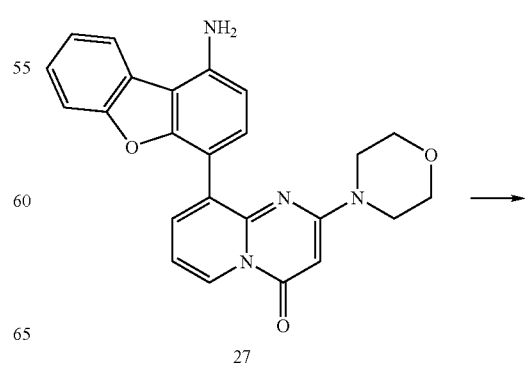

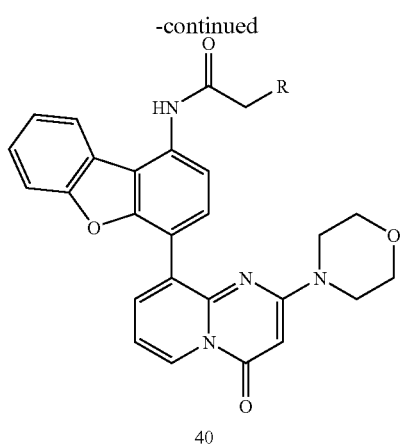

40

9-(1-Amino-dibenzofuran-4-yl)-2-morpholin-4-yl-pyrido[1,2-a]pyrimidin-4-one (27) (191 mg, 0.46 mmol) was solubilised in dry DMA (3.5 mL). Triethylamine (129 μL, 0.92 mmol) and chloroacetyl chloride (40 μL, 0.51 mmol) were added to this solution and the reaction mixture was stirred at room temperature for 4 hours. Aliquots (0.5 mL) of the resulting solution were added to 7 different tubes in a greenhouse workstation. Each tube contained a different amine (3 eq). The reaction mixtures were stirred in parallel at room temperature for 18 h. Each tube was diluted with the minimum amount of methanol (max. 1.5 mL) and transferred into a LC-MS vial. All the LC-MS vials were submitted for QC and semi-preparative HPLC for purification.

| Compound | R | Purity (%) | RT (s) | Mass (M + H) |
|---|---|---|---|---|
| 40a | *-N(morpholine) | 90 | 7.40 | 540.5 |
| 40b | *-N(N-methylpiperazine) | 78 | 7.03 | 553.5 |
| 40c | *-N(2,6-dimethylmorpholine) | 86 | 8.32 | 568.5 |
| 40d | *-N(N-ethylpiperazine) | 92 | 7.22 | 567.5 |
| 40e | *-N(N-(2-hydroxyethyl)piperazine) | 86 | 6.96 | 583.5 |
| 40f | *-N(N-(isopropylcarbamoylmethyl)piperazine) | 92 | 7.55 | 638.5 |

Example 8

Synthesis of 3-amino-N-[4-(2-morpholin-4-yl-4-oxo-4H-pyrido[2,1-a]pyrimidin-9-yl)-dibenzofuran-1-yl]-propionamides (41)

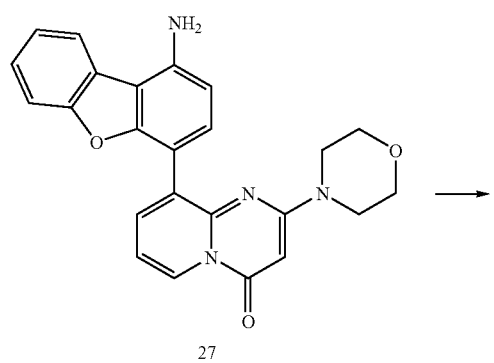

27

↓

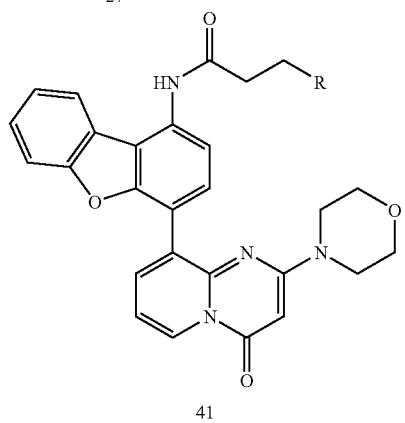

41

9-(1-Amino-dibenzofuran-4-yl)-2-morpholin-4-yl-pyrido[1,2-a]pyrimidin-4-one (27) (147 mg, 0.36 mmol) was solubilised in dry DMA (3 mL). Triethylamine (99 µL, 0.71 mmol) and 3-chloropropionyl chloride (37 µL, 0.39 mmol) were added to this solution and the reaction mixture was stirred at room temperature for 4 hours. Aliquots (0.5 mL) of the resulting solution were added to 6 different tubes in a greenhouse workstation. Each tube contained a different amine (3 eq). The reaction mixtures were stirred in parallel at room temperature for 18 h. Each tube was diluted with the minimum amount of methanol (max. 1.5 mL) and transferred into a LC-MS vial. All the LC-MS vials were submitted for QC and semi-preparative HPLC for purification.

| Compound | R | Purity (%) | RT (s) | Mass (M + H) |
|---|---|---|---|---|
| 41a | *–N(morpholine) | 91 | 7.06 | 554.5 |
| 41b | *–N(piperidine) | 94 | 7.40 | 552.5 |
| 41c | *–N(2,6-dimethylmorpholine) | 91 | 7.56 | 582.5 |
| 41d | *–NH–CH2–(tetrahydrofuran-2-yl) | 92 | 7.46 | 568.5 |

Example 9

Synthesis of 2-amino-N-[4-(2-morpholin-4-yl-4-oxo-1,4-dihydro-quinolin-8-yl)-dibenzofuran-1-yl]-acetamides (42)

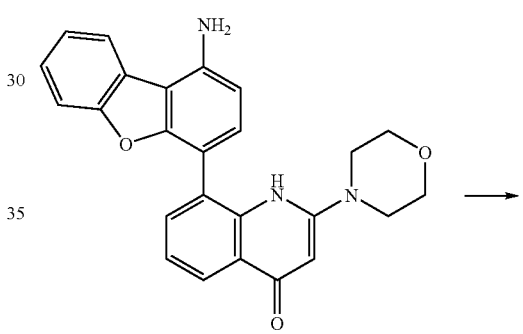

29

↓

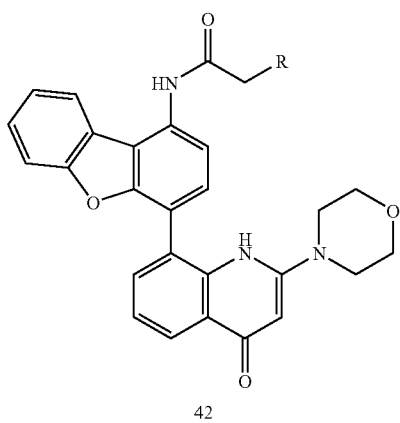

42

8-(1-Amino-dibenzofuran-4-yl)-2-morpholin-4-yl-1H-quinolin-4-one (29) (126 mg, 0.31 mmol) was solubilised in dry DMA (3.5 mL). Triethylamine (85 µL, 0.61 mmol) and chloroacetyl chloride (27 µL, 0.34 mmol) were added to this solution and the reaction mixture was stirred at room temperature for 4 hours. Aliquots (0.5 mL) of the resulting solution were added to 7 different tubes in a greenhouse workstation. Each tube contained a different amine (3 eq). The reaction mixtures were stirred in parallel at room temperature for 18 hours. Each tube was diluted with the minimum amount of methanol (max. 1.5 mL) and transferred into a LC-MS vial. All the LC-MS vials were submitted for QC and semi-preparative HPLC for purification.

| Compound | R | Purity (%) | RT (s) | Mass (M + H) |
|---|---|---|---|---|
| 42a | *–N(morpholine) | 98 | 7.07 | 539.4 |
| 42b | *–N(piperazine)–CH2CH2OCH3 | 94 | 6.96 | 596.5 |
| 42c | *–N(piperazine)–CH3 | 90 | 6.72 | 552.5 |
| 42d | *–N(2,6-dimethylmorpholine) | 92 | 7.87 | 567.5 |
| 42e | *–N(piperazine)–Et | 98 | 6.87 | 566.5 |
| 42f | *–N(piperazine)–CH2CH2OH | 100 | 6.61 | 582.5 |
| 42g | *–N(piperazine)–CH2C(O)NH-iPr | 91 | 7.20 | 637.5 |

Example 10

Synthesis of 3-amino-N-[4-(2-morpholin-4-yl-4-oxo-1,4,4a,8a-tetrahydro-quinolin-8-yl)-dibenzofuran-1-yl]-propionamides (43)

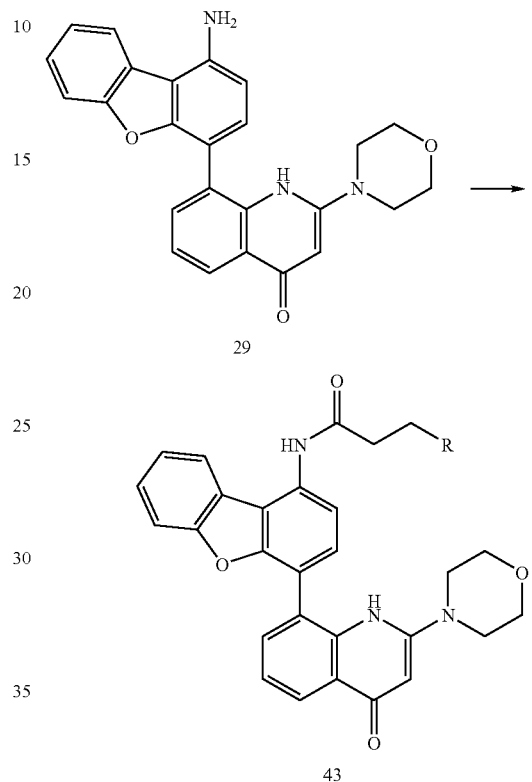

8-(1-amino-dibenzofuran-4-yl)-2-morpholin-4-yl-1H-quinolin-4-one (29) (115 mg, 0.28 mmol) was solubilised in dry DMA (3 mL). Triethylamine (78 µL, 0.56 mmol) and 3-chloropropionyl chloride (29 µL, 0.31 mmol) were added to this solution and the reaction mixture was stirred at room temperature for 4 h. Aliquots (0.5 mL) of the resulting solution were added to 6 different tubes in a greenhouse workstation. Each tube contained a different amine (3 eq); The reaction mixtures were stirred in parallel at room temperature for 18 h. Each tube was diluted with the minimum amount of methanol (max. 1.5 mL) and transferred into a LC-MS vial. All the LC-MS vials were submitted for QC and semi-preparative HPLC for purification.

| Compound | R | Purity (%) | RT (s) | Mass (M + H) |
|---|---|---|---|---|
| 43a | *–N(piperidine) | 98 | 7.05 | 551.5 |

-continued

| Compound | R | Purity (%) | RT (s) | Mass (M + H) |
|---|---|---|---|---|
| 43b | 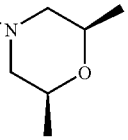 | 98 | 7.18 | 581.5 |

Example 11

Synthesis of 2-amino-N-[4-(2-morpholin-4-yl-1-benzopyran-4-one)-dibenzofuran-1-yl]-acetamides (44)

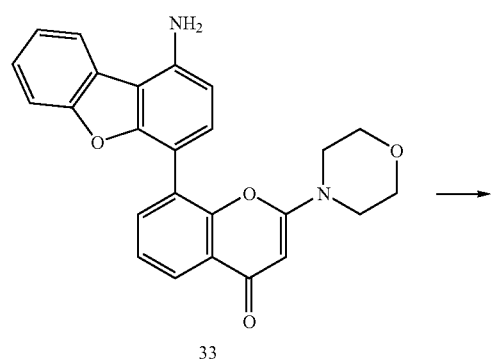

33

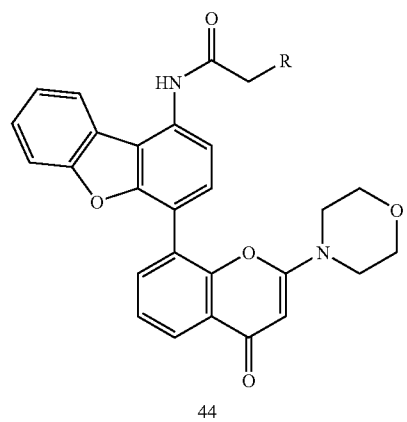

44

To a solution of 8-(1-amino-dibenzofuran-4-yl)-2-morpholin-4-yl-1-benzopyran-4-one (1 equivalent in chloroform (0.02M) was added sodium carbonate (2 equivalents) then chloroacetyl chloride (1.1 equivalents). The mixture was stirred at room temperature for 4 hours before the addition of the appropriate amine (1.2 equivalents). The reaction was heated to 60° C. for 24 hours before being concentrated in vacuo and then purified by preparative HPLC to give the desired product.

| Compound | R | Purity (%) | RT (s) | Mass (M + H) |
|---|---|---|---|---|
| 44a |  | 98 | 4.00 | 554.1 |
| 44b |  | 99 | 4.08 | 540.1 |
| 44c |  | 100 | 4.47 | 568.5 |
| 44d |  | 99 | 4.06 | 567.6 |

Example 12

Synthesis of Synthesis of 3-amino-N-[4-(2-morpholin-4-yl-1-benzopyran-4-one)-dibenzofuran-1-yl]-propionamides (45)

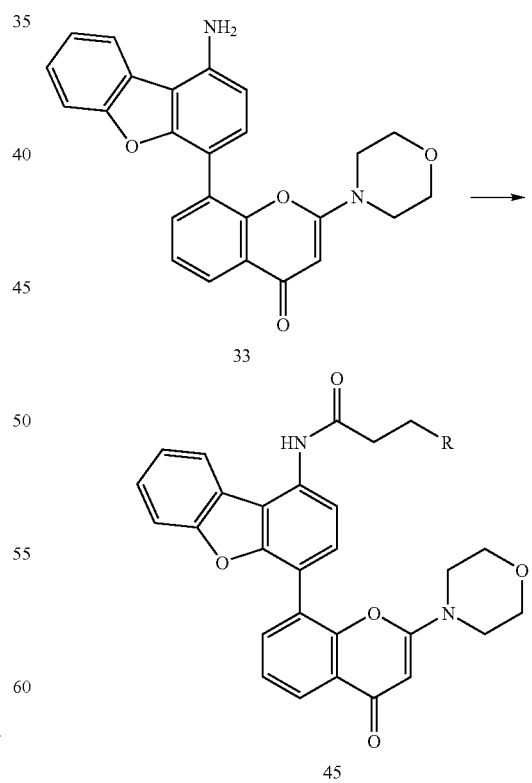

To a solution of 8-(1-amino-dibenzofuran-4-yl)-2-morpholin-4-yl-1-benzopyran-4-one (1 equivalent in chloroform (0.02M) was added sodium carbonate (2 equivalents) then bromopropionyl chloride (1.1 equivalents). The mixture was stirred at room temperature for 4 hours before the addition of the appropriate amine (1.2 equivalents). The reaction was heated to 60° C. for 24 hours before being concentrated in vacuo and then purified by preparative HPLC to give the desired product.

| Compound | R | Purity (%) | RT (s) | Mass (M + H) |
|---|---|---|---|---|
| 45a | 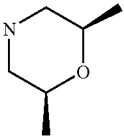 | 99 | 4.13 | 582.6 |
| 45b | 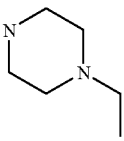 | 99 | 3.92 | 581.6 |
| 45c | 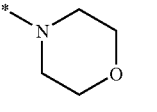 | 99 | 3.99 | 554.6 |
| 45d | 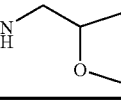 | 94 | 4.1 | 568.6 |

Biological Examples

DNA-PK Inhibition

In order to assess the inhibitory action of the compounds against DNA-PK in vitro, the following assay was used to determine $IC_{50}$ values.

Mammalian DNA-PK (500 ng/ml) was isolated from HeLa cell nuclear extract (Gell, D. and Jackson S. P., *Nucleic Acids Res.* 27:3494-3502 (1999)) following chromatography utilising Q-sepharose, S-sepharose and Heparin agarose. DNA-PK (250 ng) activity was measured at 30° C., in a final volume of 40 µl, in buffer containing 25 mM Hepes, pH7.4, 12.5 mM $MgCl_2$, 50 mM KCl, 1 mM DTT, 10% Glycerol, 0.1% NP-40 and 1 mg of the substrate GST-p53N66 (the amino terminal 66 amino acid residues of human wild type p53 fused to glutathione S-transferase) in polypropylene 96 well plates. To the assay mix, varying concentrations of inhibitor (in DMSO at a final concentration of 1%) were added. After 10 minutes of incubation, ATP was added to give a final concentration of 50 µM along with a 30 mer double stranded DNA oligonucleotide (final concentration of 0.5 ng/ml) to initiate the reaction. After 1 hour with shaking, 150 µl of phosphate buffered saline (PBS) was added to the reaction and 5 µl then transferred to a 96 well opaque white plate containing 45 µl of PBS per well where the GSTp53N66 substrate was allowed to bind to the wells for 1 hour. To detect the phosphorylation event on the serine 15 residue of p53 elicited by DNA-PK a p53 phospho-serine-15 antibody (Cell Signaling Technology) was used in a basic ELISA procedure. An anti-rabbit HRP conjugated secondary antibody (Pierce) was then employed in the ELISA before the addition of chemiluminescence reagent (NEN Renaissance) to detect the signal as measured by chemiluminescent counting via a TopCount NXT (Packard).

The enzyme activity for each compound is then calculated using the following equation:

$$\% \text{ Inhibition} = 100 - \left( \frac{(cpm \text{ of unknown} - \text{mean negative } cpm) \times 100}{(\text{mean positive } cpm - \text{mean negative } cpm)} \right)$$

The results are discussed below as $IC_{50}$ values (the concentration at which 50% of the enzyme activity is inhibited). These are determined over a range of different concentrations, normally from 10 µM down to 0.001 µM. Such $IC_{50}$ values are used as comparative values to identify increased compound potencies.

Survival Enhancement Ratio

The Survival Enhancement Ratio (SER) is a ratio of the enhancement of cell kill elicited by the DNA-PK inhibitor after 2 Grays of irradiation compared to unirradiated control cells. DNA-PK inhibitors were used at a fixed concentration of 500 nM. Radiation was delivered by a Faxitron 43855D machine at a dose rate of 1 Gy pre minute The SER at 2 Gray irradiation was calculated from the formula:

$$SER = \frac{\text{Cell survival in presence of } DNA - PK \text{ inhibitor}}{\text{Cell survival of control cells}} \times \frac{\text{Cell survival after } IR}{\text{Cell survival after } IR \text{ in presence of } DNA - PK \text{ inhibitor}}$$

The degree of cell killing was monitored by a standard clonogenic survival assay. Briefly, tissue culture treated 6-well plates were seeded with HeLa cells at an appropriate concentration to give 100-200 colonies per well and returned to the incubator in order to allow the cells to attach. Four hours later, compound or vehicle control was added to the cells. The cells were then incubated for 1 hour in the presence of inhibitor prior to irradiation at 2 Gray using a Faxitron 43855D cabinet X-ray machine. The cells were then incubated for a further 16 hours before the media was replaced with fresh media in the absence of DNA-PK inhibitor. After 8 days, colonies formed were fixed and stained with Giemsa (Sigma, Poole, UK) and scored using an automated colony counter (Oxford Optronics Ltd, Oxford, UK). The data was calculated as described above.

Results

All the compounds showed activity in DNA-PK inhibition, exhibiting an $IC_{50}$ of less than about 500 nM.

Compounds which exhibited particular efficacy in DNA-PK inhibition, having an $IC_{50}$ of less than about 100 nM include 23, 25, 31, 34b, 35a-b, 36a-d, 36f-k, 37b-e, 38b, 38d-h, 39d-f, 40a-f, 41a-d, 42b, 42d, 42f, 44a-d, 45a, 45c.

All the compounds showed an SER of 1 or more. Compounds with an SER of 2 or more included the following: 22, 23, 24, 25, 31, 36a-k, 37a-c, 37e, 38a-h, 39a-f.

The invention claimed is:

1. A compound of formula (I):

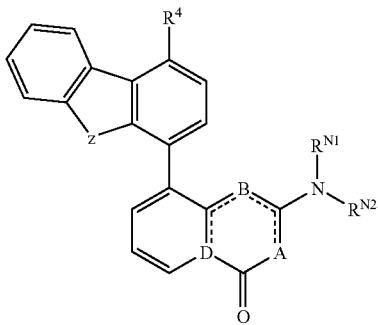

and isomers, salts, chemically protected forms, or prodrugs thereof, wherein, A, B and D are respectively selected from the group consisting of:
(i) CH, NH, C;
(ii) CH, N, N; and
(iii) CH, O, C;
the dotted lines represent two double bonds in the appropriate locations;
$R^{N1}$ and $R^{N2}$ are independently selected from hydrogen, an optionally substituted $C_{1-7}$ alkyl group, $C_{3-20}$ heterocyclyl group, or $C_{5-20}$ aryl group, or together form, along with the nitrogen atom to which they are attached, an optionally substituted heterocyclic ring having from 4 to 8 ring atoms;
if A, B, D are selected from groups (i), (ii) above, then Z is selected from the group consisting of S, O, C(=O), $CH_2$ and NH; and if A, B, D represent group (iii), then Z is selected from the group consisting of O, C(=O), $CH_2$ and NH;
$R^4$ is selected from the group consisting of H, OH, $NO_2$, $NH_2$ and Q—Y—X where
Q is —NH—C(=O)— or —O—;
Y is an optionally substituted $C_{1-15}$ alkylene group;
X is selected from $SR^{S1}$ or $NR^{N3}R^{N4}$, wherein,
$R^{S1}$, or $R^{N3}$ and $R^{N4}$ are independently selected from hydrogen, optionally substituted $C_{1-7}$ alkyl, $C_{5-20}$ aryl, or $C_{3-20}$ heterocyclyl groups, or $R^{N3}$ and $R^{N4}$ together form, along with the nitrogen atom to which they are attached, an optionally substituted heterocyclic ring having from 4 to 8 ring atoms;
if Q is —O—, then X may additionally be selected from —C(=O)—$NR^{N5}R^{N6}$, wherein $R^{N5}$ and $R^{N6}$ are independently selected from hydrogen, optionally substituted $C_{1-7}$ alkyl, $C_{5-20}$ aryl, or $C_{3-20}$ heterocyclyl groups, or $R^{N5}$ and $R^{N6}$ together form, along with the nitrogen atom to which they are attached, an optionally substituted heterocyclic ring having from 4 to 8 ring atoms and
if Q is —NH—C(=O)—, then —Y—X may additionally be selected from $C_{1-7}$ alkyl;
with the proviso that if A, B, D represent group (iii) and $R^{N1}$ and $R^{N2}$ together with the carbon atom to which they are bound form a morpholino group, $R^4$ cannot be H.

2. A compound according to claim 1, wherein $R^4$ is Q-Y—X.

3. A compound according to claim 1, wherein Q is —NH—C(=O)— and X is $NR^{N3}R^{N4}$.

4. A compound according to claim 1, wherein Q is —O—, X is $NR^{N3}R^{N4}$, and Y is an optionally substituted $C_{1-3}$ alkylene group.

5. A compound according to claim 1, wherein Z is selected from S and O, where appropriate.

6. A compound according to claim 1, wherein $R^{N1}$ and $R^{N2}$ form, along with the nitrogen atom to which they are attached, a heterocyclic ring having from 4 to 8 atoms.

7. A compound according to claim 1, wherein $R^{N1}$ and $R^{N2}$ form, along with the nitrogen atom to which they are attached, a group selected from morpholino and thiomorpholino.

8. A composition comprising a compound according to claim 1, and a pharmaceutically acceptable carrier or diluent.

9. A method of inhibiting DNA-PK in vitro or in vivo, comprising contacting a cell with an effective amount of a compound according to claim 1.

* * * * *